US005693767A

United States Patent [19]
Klemke et al.

[11] Patent Number: 5,693,767
[45] Date of Patent: Dec. 2, 1997

[54] GLYCOSIDE DERIVATIVES OF ACETAMINOPHEN

[75] Inventors: R. -Erich Klemke, Hilzingen, Germany; Masato Koreeda, Ann Arbor, Mich.; Todd A. Houston, Timonium, Md.; Brian K. Shull, Ann Arbor; Roeland J. Tuinman, Fenton, both of Mich.

[73] Assignee: Harrier Inc., Hermosa Beach, Calif.

[21] Appl. No.: 251,869

[22] Filed: Jun. 1, 1994

Related U.S. Application Data

[63] Continuation-in-part of Ser. No. 6,447, Jan. 21, 1993, abandoned, which is a continuation-in-part of Ser. No. 815,691, Jan. 24, 1992, abandoned, which is a continuation-in-part of Ser. No. 733,915, Jul. 22, 1991, abandoned, which is a continuation-in-part of Ser. No. 644,002, Jan. 22, 1991, Pat. No. 5,278,296.

[51] Int. Cl.$^6$ ............... C07H 15/20; A61K 31/70
[52] U.S. Cl. ............... 536/4.1; 514/23; 514/25; 536/18.5; 536/18.6
[58] Field of Search ............... 536/5, 4.1, 17.2, 536/18.1, 18.5, 18.6, 123.13; 514/25, 26, 53, 169, 183, 449, 553, 576, 23

[56] References Cited

U.S. PATENT DOCUMENTS

| 3,857,832 | 12/1974 | Harlenstein | 260/210.5 |
|---|---|---|---|
| 3,859,047 | 1/1975 | Klein | 23/230 B |
| 4,157,391 | 6/1979 | Kilame et al. | 424/238 |
| 4,402,948 | 9/1983 | Matsumura | 424/182 |
| 5,126,437 | 6/1992 | Tietze et al. | 536/17.1 |

FOREIGN PATENT DOCUMENTS 3127933  8/1982  Germany .

OTHER PUBLICATIONS

Ferrier, J. Chem. Soc. (1962), "The Reaction Between 3,4,6-Tri-O-Acetyl-D-Glucal and p-Nitrophenol," 3667-3670.

Ferrier, "Unsaturated Sugars," Adv. Carbohydrate Chemistry, 20, pp. 90-91 (1965).

Ferrier, J. Chem. Soc., (1969) "Unsaturated Carbohydrates," 570-575.

Honda, Carbohydrate Research, 29 (1973), "Preparation of O-(2-deoxy-α-D-arabino-hexopyranosyl)-(1-6)-D-glucose by oxyiodination-hydrogenation method", pp. 488-491.

Garegg, Carbohydrate Research, 92 (1981), "Novel Glycosylation Reagents: synthesis of disaccharides containing 2-deoxy-2-iodo-α-D-talopyranosyl groups", pp. 157-159.

C.A. 97:6734s. Nitrosourea derivatives.

Thiem, Liebigs Ann. Chem. 1985, "Untersuchungen aur Darstellung von Desoxyzuker–Steroidglysosiden", pp. 2135-2150.

Steinkellner, ORTHOMolecular (1989), "Tumosteron Behandeling Van Kanker", pp. 206-211.

Bolitt, J. Org. Chem. 1990, SS, "Direct Preparation of 2-Deoxy-D-glucopyranosides from Glucals without Ferrier Rearrangement", pp. 5812-5813.

Primary Examiner—John Kight
Assistant Examiner—Howard C. Lee
Attorney, Agent, or Firm—Medlen & Carroll, LLP

[57] ABSTRACT

Novel glycosides, especially steroidal and non-steroidal glycosides are provided. The steroidal and non-steroidal glycosides preferably are prepared from aglycons which possess valuable properties such as pharmacological properties. The glycosides are prepared from useful aglycons and possess useful properties which are the same as those of their respective unglycosylated aglycons. The glycosides are provided in acylated and deacylated form. The acylated glycosides after hydrolysis of the acyl groups possess enhanced water solubility properties, as illustrated in the case where the aglycon is acetominophen.

8 Claims, 8 Drawing Sheets

GLYCOSIDE DERIVATIVES OF ACETAMINOPHEN

PRIOR APPLICATIONS

This is a continuation-in-part of U.S. application Ser. No. 08/006,447, filed Jan. 21, 1993, now abandoned which is a continuation-in-part of U.S. application Ser. No. 815,691 filed Jan. 24, 1992, now abandoned, which is a continuation-in-part of U.S. Ser. No. 733,915 filed Jul. 22, 1991, now abandoned, which is a continuation-in-part of U.S. application Ser. No. 644,002 filed Jan. 22, 1991, issued Jan. 11, 1994 as U.S. Pat. No. 5,278,296.

FIELD OF THE INVENTION

This invention relates to a surprisingly novel method for the production of a broadly novel type of glycosides. The method comprises glycosylation (i.e., glycosidation) of an aglycon compound having a functional group, e.g., a hydroxy compound such as a hydroxy-steroid or hydroxy-non-steroid. The invention also importantly relates to the resulting glycosides as novel compounds of diverse application having desired properties including pharmacodynamic properties; and to medicaments containing the compounds.

The glycosylation of alcohols or phenols and particularly glycosylation of hydroxy-steroids, is known per se. However, glycosylation often produces undesired ortho esters as described, e.g., in Chemical Abstracts, Vol. 105, 1986, 172882s. A method which minimizes the content of the unwanted ortho ester is disclosed in Chemical Abstracts, Vol. 104, 1986, 22511g (Liebigs Ann. Chem. 1986, 717–730). However, this method again does not completely avoid the formation of ortho esters. Further, the method requires the use of pivaloylglucopyranosylbromide wherein the pivaloyl groups function as protecting groups to suppress the formation of ortho esters. The reaction of the glycoside with the steroid proceeds by means of silver oxide or silver carbonate catalysts.

The use of α-halo tetraacetylglucosides which are commonly used for the glycosylation of steroids, especially of cholesterol, requires the use of expensive or toxic reaction catalysts, such as $Ag_2O$, $Ag_2CO_3$, $PbCO_3$, $Hg(CN)_2$, etc. This as a practical matter prohibits its technical application on a large scale. Furthermore, these glycosylation procedures generally constitute multistage processes which also lead to an unwanted mixture of α- and β-glycosylation.

One object of the present invention is to provide a convenient method for the production of glycosides. Another object of the invention is to provide novel glycosides of known aglycons for their known use as aglycons, especially steroidal and non-steroidal glycosides as well as therapeutically-active agents, especially glycosides that possess enhanced water-solubility, vis-a-vis their aglycons. Still another object is to provide novel steroidal and non-steroidal derivative glycosides of known aglycons having utility and useful properties, especially pharmacological properties as detailed and referenced herein, for prevention, treatment or control of disease in mammals. Thus, the known aglycons are useful as human and veterinary medicinal products of known posology. Representative, preferred aglycons and their respective medicinal uses are listed below at paragraphs a) to r).

This invention serves as an ideal way of providing novel glycosides, especially steroidal and non-steroidal glycosides that are useful for pharmacological applications. The glycosylation employs known starting materials and proceeds in one step without special laboratory measures such as nitrogen gassing and/or operation at extreme temperatures. The glycosylation avoids the use of halogenated glycosides and toxic catalysts, such as $Ag_2O$, $Ag_2CO_3$, $PbCO_3$, $Hg(CN)_2$, etc. The glycosylation also avoids the formation of ortho esters.

It has been surprisingly found according to the invention that an aglycon compound—in a preferred embodiment, a hydroxy-steroid to be understood as a steroidal alcohol or steroidal phenol—can be reacted in one step with a glycosidic vinyl ether 3,4,6-tri-O-acyl-D-glucal of formula

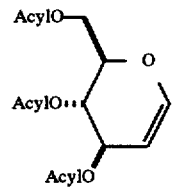

where Acyl is a lower aliphatic acyl group or aromatic acyl group, e.g., a $C_{1-4}$ acyl group or a substituted or unsubstituted benzoyl group, in the presence of molecular halogen as a catalyst, such as iodine $I_2$, chlorine $Cl_2$, bromine $Br_2$ and fluorine $F_2$, preferably iodine, to provide the corresponding glycoside in high yield. Thus there is no need for expensive and/or toxic reagents in this reaction step. Further, as a preferred aspect of the invention, a steroidal glycoside—a 7β-hydroxycholesterol 3-pyranoside which is 7β-hydroxycholesteryl 2,3-dideoxy-α-D-erythro-hex-2-enopyranoside (FIGS. 6 and 7 herein), obtainable by this method—has been found to be applicable as a pharmacologically active agent for use as a medicament, especially as an anti-neoplastic agent, or in geriatric medicine, or as a sedative or activity-enhancing agent. For convenience in describing the invention, the term 4,6-di-O-acyl (or acetyl) -2,3-dideoxy-α-D-erythro-hex-2-enopyranoside will sometimes be referred to herein simply as DDH pyranoside.

In the accompanying drawings with reference to preferred examples of the invention:

DETAILED DESCRIPTION OF THE EMBODIMENTS

Figure 1:
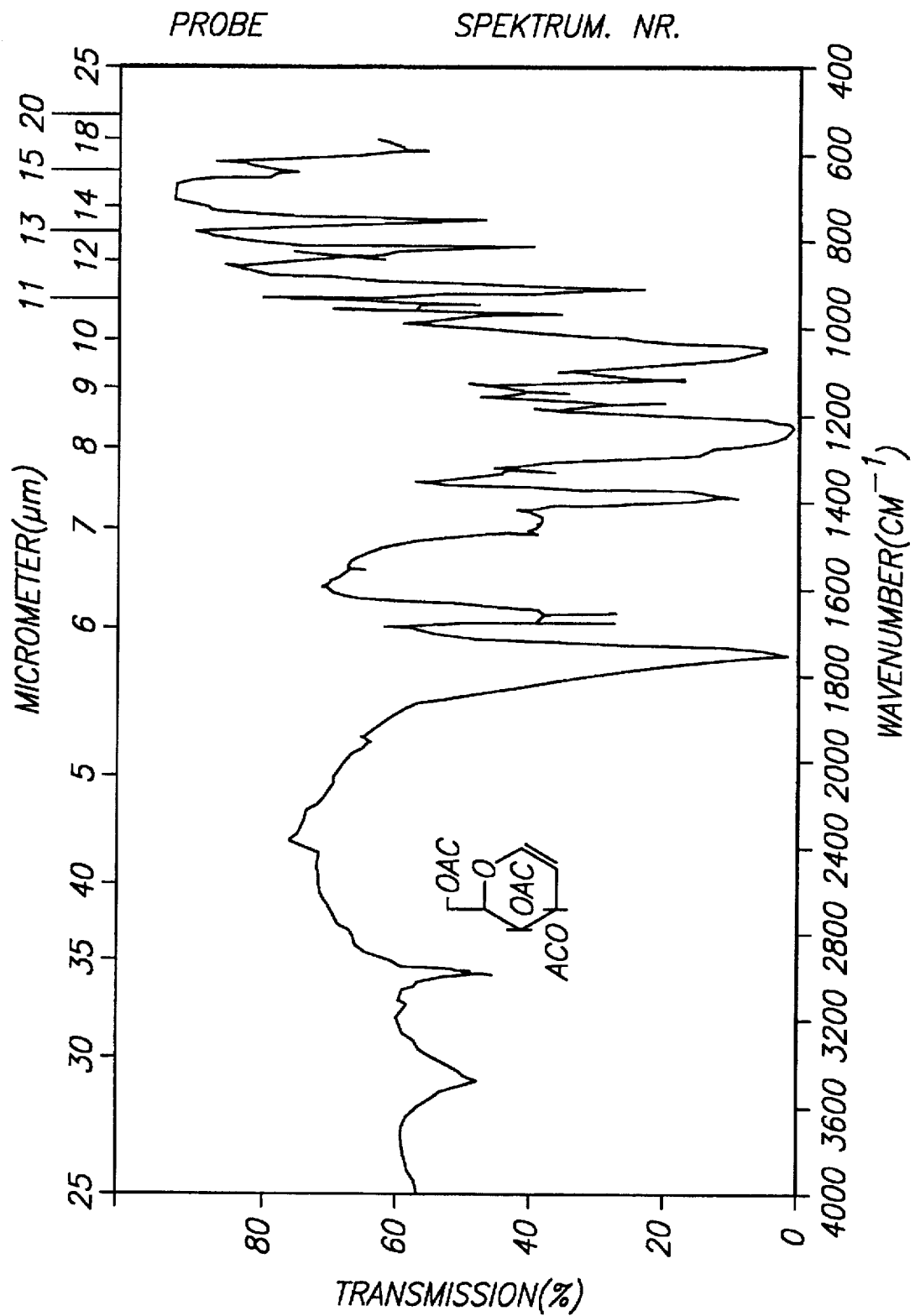
FIG. 1 is an infrared spectrum of the glucal used in the reaction of Example 1.

According to one preferred embodiment, the invention concerns a method for the production of a pyranoside compound, wherein an aglycon compound selected from aliphatic, alicyclic, aliphatic-aromatic or aromatic compounds having a primary, secondary or tertiary functional group preferably selected from —OH, —SH, and —COOH, is glycosylated. In this method the aglycon compound is reacted in a solvent with a 3,4,6-tri-O-acyl-glucal of formula

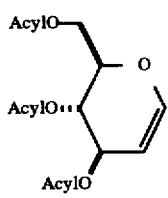

3

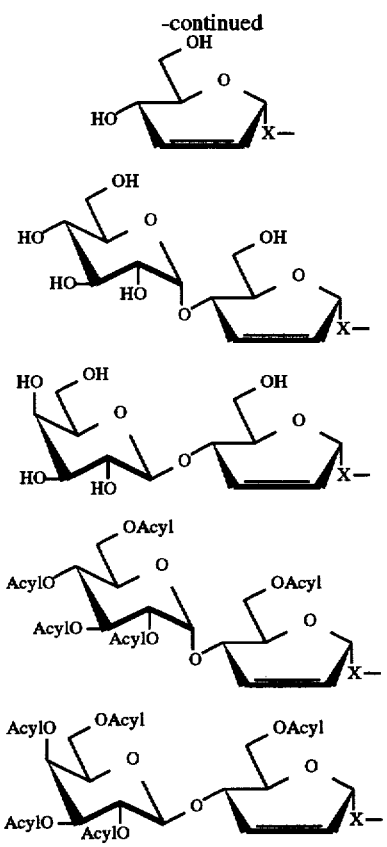

4

(for example, 3,4,6-tri-O-acetyl-D-glucal made from acetobrom-α-O-glucose in acetic acid and reduction with fine dispersed zinc, Emil Fischer, 1914; or a mono or poly glycosylate thereof or an analogous compound made from the corresponding acetylated $C_1$-α-Br mannose or allose) in the presence of molecular or ionized halogen as a catalyst, such as iodine $I_2$, chlorine $Cl_2$, bromine $Br_2$, and fluorine $F_2$, preferably iodine, to produce the corresponding 4,6-di-O-acyl-2,3-dideoxy-α-D-erythro-hex-2-enopyranoside of said aglycon compound, where acyl is as defined above. In another preferred embodiment a hydroxysteryl compound, preferably a 3β-hydroxysterol compound, more preferably a 5-en-3β-ol steroid compound such as cholesterol (i.e., 5-cholesten-3β-ol), is glycosylated by reaction with 3,4,6-tri-O-acyl-D-glucal in a solvent in the presence of molecular halogen, preferably iodine, as a catalyst. Alternatively, a non-steroidal compound can be thus glycosylated as detailed herein. The reaction is achieved in a single step and in high yield. Thus a double bond is introduced between $C_2$ and $C_3$ of the glycosidic part of the molecule, whereby as to the hydroxysteryl compound the delta[5] double bond of the cyclopentano-perhydrophenanthrene skeleton remains unchanged.

Furthermore, the invention comprises the use of the resulting unsaturated glycoside obtained as an end product or as an intermediate in further reactions to provide functional derivatives which may be steroidal, e.g., cholesterol, or non-steroidal derivatives. Thus, in the case of cholesterol, functional groups can be introduced into the perhydrocyclopentanophenanthrene skeleton of the unsaturated acylglycoside, wherein the α-bond of the acylglycoside at the same time functions as a protecting group for the original OH-group at $C_3$ of the perhydrophenanthrene skeleton.

Non-steroidal derivatives according to a preferred embodiment of the invention are detailed in the following description. These non-steroidal derivatives and the steroidal derivatives of the invention can each be obtained either in peracylated form or, for enhanced water-solubility, in partly or completely deacylated form by removal of one or more acyl groups to provide after workup the desired corresponding hydroxy derivative.

Thus, the invention comprises a glycoside derivative of an aglycon selected from aliphatic, alicyclic, aliphatic-aromatic and aromatic aglycon compounds having a primary, secondary or tertiary functional group selected from the group consisting essentially of —OH, —SH, and —COOH, said glycoside derivative being selected from the group consisting of mono- and disaccharides having a 2,3-dideoxy-α-D-erythro-hex-2-enopyranoside moiety of the formulas A, B, C, D, E and F:

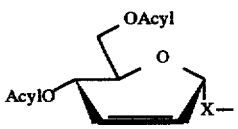

where Acyl is a lower aliphatic acyl group or an aromatic acyl group, and X is selected from —O—, —S—, and —OCO—, provided however that said aglycon is not cholesterol.

Also, the invention comprises in another preferred embodiment, a method of deacylating the acylated glycoside derivative. This is accomplished by hydrolysis of one or more acyl groups from the acylated product. For hydrolysis, acyl group removal can be achieved for example by refluxing the acylated product, under per se commonly used conditions for hydrolysis and workup, with an aqueous metal hydroxide [M(OH)$_n$; e.g., M=Li, K, Na, Ba] in methanol, ethanol or THF, or with Zn $(OAc)_2.2H_2O$ in methanol, or with $LiAlH_4$ or diisobutylaluminium hydride in benzene, toluene, ether or THF.

The present method is in contrast to the analytical procedure for the iodometric assay of vinyl ethers by ionized iodine in alcohol with formation of the corresponding iodoacetals according to S. Siggia and R. L. Edsberg, Ind. Eng. Chem. Anal. 20, 762 (1948), thereby using ionized iodine in the reaction. By contrast, the method according to a preferred embodiment of this invention makes use of iodine which is molecularly dissolved in inert solvents. These inert solvents, for example, comprise $CH_2Cl_2$ dichloromethane, $CHCl_3$ chloroform, $CCl_4$ carbon tetrachloride, $C_6H_4(CH_3)_2$ xylene, $C_6H_3(CH_3)_3$ mesitylene, $C_6H_5CH(CH_3)_2$ cymene, $C_6H_{12}$ cyclohexane and methyl derivatives thereof, as well as ligroin, petroleum ether and saturated hydrocarbons, such as for example n-pentane or n-heptane, preferably $C_6H_6$ benzene or $C_6H_5CH_3$ toluene. Using the alternative solvent nitromethane $CH_3NO_2$, the glycosylation reaction catalyzed by iodine runs quantitatively at room temperature in 2 hours. The method of the invention for the preparation of the DDH pyranoside also makes use of iodine dissolved in the following ketonic solvents. Thus, using acetone, methyl ethyl ketone (2-butanone), or cyclohexanone as an alternative solvent, the iodine-catalyzed reaction between 3,4,6-tri-O-acetyl-D-glucal and cholesterol runs quantitatively at 20° C. in only 60 to 90 minutes. As a preferred embodiment, one can also use tetrahydrofuran (THF), ethers and the like.

In contrast to the work of Siggia et al., supra, producing iodoacetals, the iodine-catalyzed reaction with 3,4,6-tri-O-acetyl-D-glucal generates the usual unsaturated sugar residue in accordance with this invention.

The glycosylation method according to the mentioned preferred embodiment is directed to the reaction of the vinyl ether of 3,4,6-tri-O-acyl-D-glucal with a cholesterol such as 5-cholesten-3β-ol, with molecularly dissolved halogen, i.e. iodine, as catalyst in one of the aforementioned solvents. The reaction thereby introduces a double bond between C-atoms 2 and 3, while eliminating the acyl group sited at $C_3$, instead of introducing an iodine atom at $C_2$ in the glycosidic part of the resulting cholesteryl glycoside. This reaction is conveniently followed by IR-spectroscopy, and is complete only when the peak of the glucal at 1650 cm$^{-1}$ has disappeared. The iodine being utilized as catalyst is quantitatively titrated back by a suitable back-titrant reagent such as 0.1N aqueous sodium thiosulphate ($Na_2S_2O_3$). The method for providing the corresponding di-O-acyl glycoside as exemplified hereinafter for the cholesterol compound is applicable to the glycosylation of not only steroid compounds and cholesterol but also aglycon compounds in general, i.e., aliphatic, alicyclic, aliphatic-aromatic and aromatic compounds having a primary, secondary, or tertiary functional group of the type mentioned. Aglycon compounds that are useful for their pharmacological properties are preferred, since their respective glycosides produced according to the invention have the same utility and useful properties and art-recognized dosage regimens with the possible enhancement of bioavailability, e.g., at cell membranes, due to the presence of the added sugar residue. Preferred hydroxy compounds for glycosylation comprise cholesterols, bile salts, steroid hormones, and vitamin D compounds and precursors as described in Stryer's *Biochemistry*, 3rd Ed. pp. 559–570, Freeman and Company, New York, 1988, incorporated herewith by reference. Examples of such compounds are cholic acid and derivatives, 25-hydroxy-calciferol, pregnenolone, 17α-hydroxyprogesterone, 17α-hydroxypregnenolone, 11-desoxy-corticosterone, 11-desoxy-cortisol, corticosterone, cortisol, cortisone, dolichol, androsterone, testosterone, estrone, 17β-estradiol, 3,16α, 17β-estratriol, tetrahydrocorticosterone, serotonin, urocortisol, and allocortolone, and the like, preferably cyclopentanoperhydrophenanthrene compounds having the 5-en-3β-OH steryl moiety

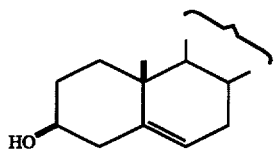

Other preferred aglycon compounds for glycosylation include a) α- and β-sympathomimetic (adrenergic) compounds such as p-hydroxyphenylethanolamine, norfenefrine, synephrine, etilefrin, phenylephrine, octapamine, isoprenaline, dichloroisoproterenol, metaproterenol, terbutaline, buphenine, and the like;

b) antihypertensive compounds such as methyldopa and the like;

c) vasoconstrictor compounds such as α-methylnoradrenaline, and the like;

d) cardiotonic compounds such as digitoxigenin, digoxigenin, diginatigenin, and the like;

e) estrogen and contraceptive compounds such as ethinylestradiol, mestranol, quinestrol, and the like;

f) antibacterial compounds such as amoxicillin, chloramphenicol, thiamphenicol, tetracycline, chlortetracycline, oxytetracycline, and the like;

g) oxytocic compounds such as prostaglandin $F_{2\alpha}$, and the like;

h) fungicidal compounds such as the plant growth regulator cycloheximide, and the like;

i) antirheumatic compounds such as oxyphenbutazone, and the like;

j) anticholelithogenic compounds such as chenodiol, and the like;

k) choleretic compounds such as hymecromone, and the like;

l) anti-parkinsonian compounds such as levodopa, carbidopa, droxidopa, and the like;

m) anti-spasmodic compounds such as ephedrine, and the like;

o) muscle relaxant compounds such as phenprobamate, guaiacol glycerol ether, mephenesin, and the like;

p) anti-inflammatory compounds such as dexamethasone, beclomethasone, and the like;

q) analgesic compounds such as acetaminophen (Tylenol®), capsaicin, and the like; and r) vitamin and vitamin related compounds such as provitamin D, xanthophyll, vitamin A, vitamin E, thiamin, ascorbic acid, and the like.

These preferred aglycon compounds for glycosylation according to the invention are listed as indexed Abstracts in The Merck Index XI, Merck & Co., Inc., Rahway, N.J., incorporated herewith by reference.

The glycosylation method and related oxidation and reduction methods described hereinafter may be illustrated by a preferred embodiment employing the starting material cholesterol, as follows:

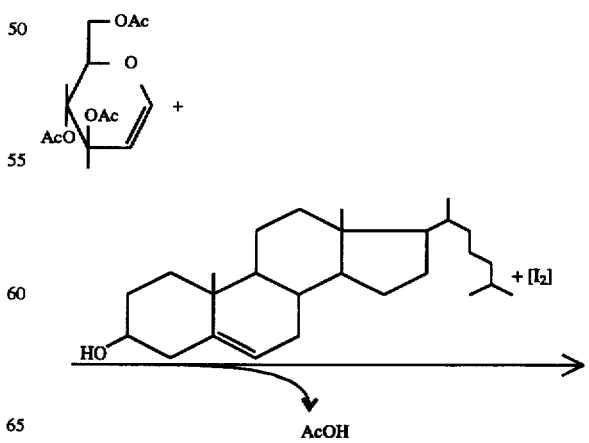

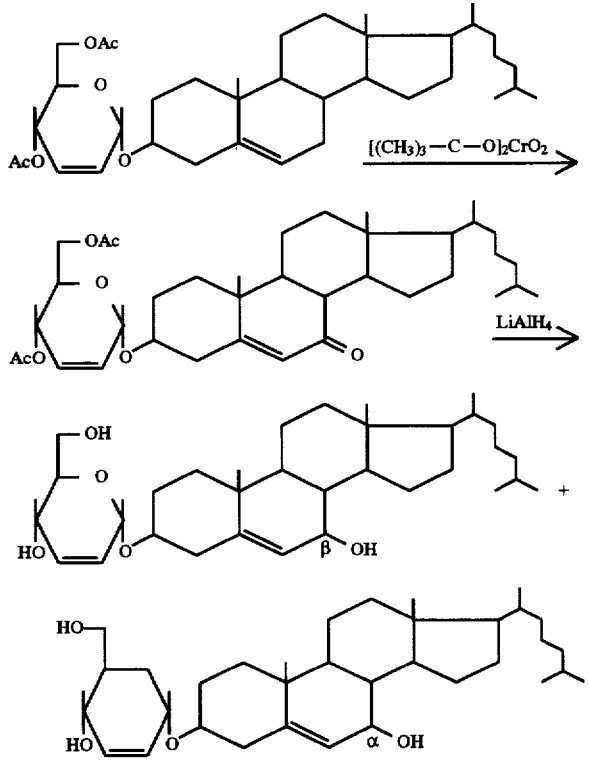

In another method aspect of the invention, the steryl DDH pyranoside product obtained by the glycosylation method can be converted by oxidation of the steroid part into an α-glycosylated 7-ketosterol such as α-glycosylated 7-ketocholesterol. The method is applicable to the oxidation of sterol compounds broadly, preferably cyclopentano-perhydrophenanthrene compounds having the 5-en-3β-OH steryl 4,6-di-O-acyl-2,3-dideoxy-α-D-erythro-hex-2-enopyranoside moiety

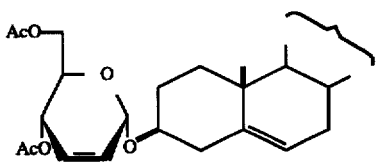

to provide the corresponding 7-keto sterols having the corresponding moiety

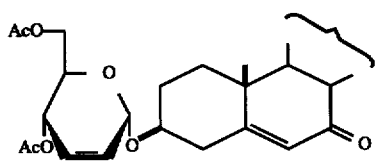

The oxidation is accomplished with an oxidizing agent, which preferably contains chromium, with pyridine-chromium trioxide $(C_5H_5N)_2CrO_3$ or pyridine-chlorochromate $(C_5H_5NHCrO_3)Cl$ being preferred and t-butyl chromate being especially preferred. The inert glycosidic double bond between $C_2$ and $C_3$ thereby remains intact. The reduction of this 7-ketone with a suitable reducing agent, preferably a complex metal hydride, such as one or more of $LiAlH_4$, $NaBH_4$, and $KBH_4$, more preferably $LiAlH_4$, leads to a steroidal glycoside according to the invention. In a preferred embodiment, the method importantly provides 7β-hydroxycholesteryl 2,3-dideoxy-α-D-erythro-hex-2-enopyranoside (7β-OHC DDH pyranoside) of formula

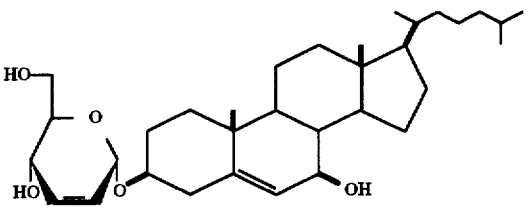

which cholesterol is systemically biocompatible. The product is obtained after workup of the reaction mixture, e.g. by chromatographic separation of the 7β-hydroxy isomer from the 7α-hydroxy isomer, in a suitable solvent mixture, preferably a mixture comprising dichloromethane:acetone, preferably in 1:1 mixture.

Figure 8:
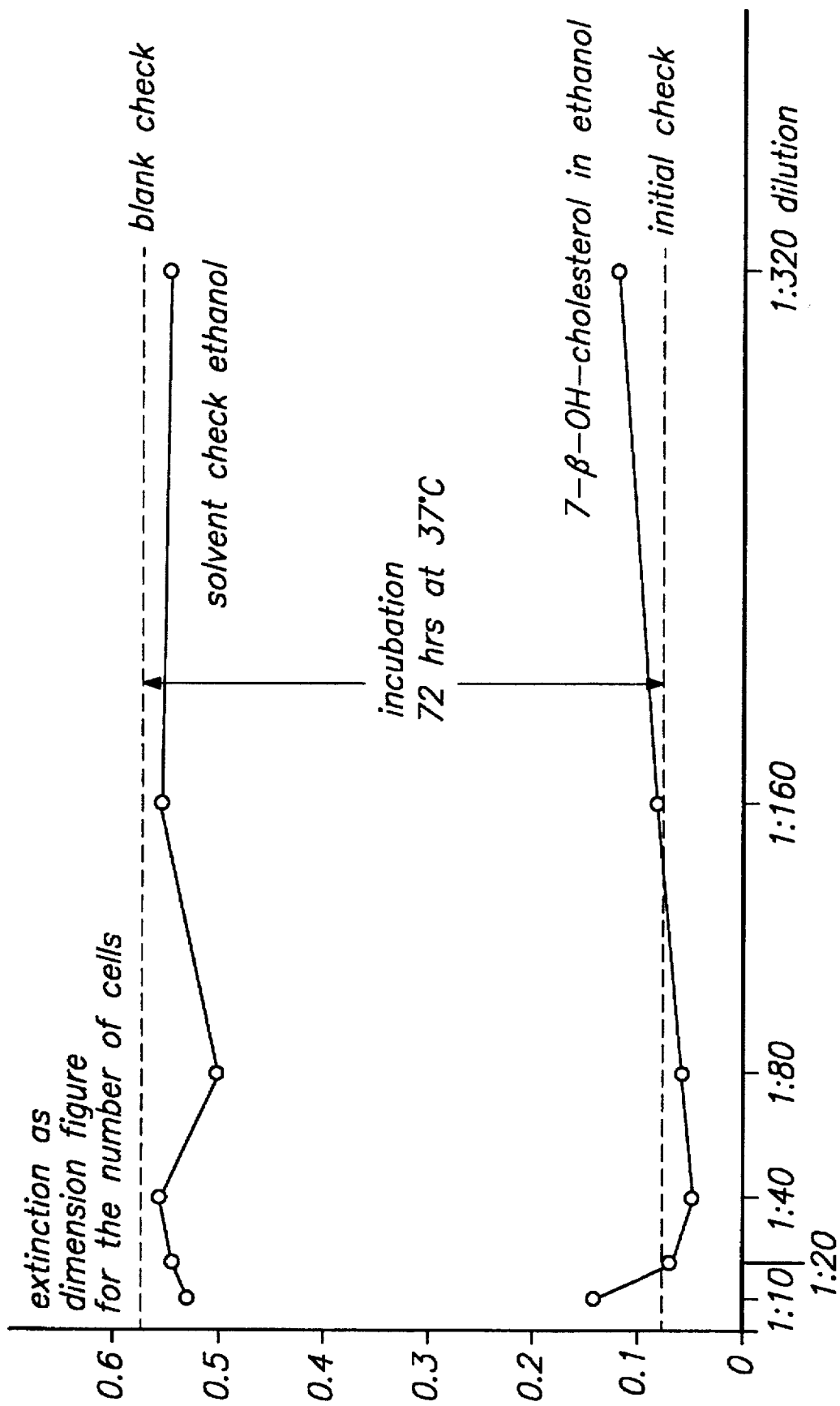
FIG. 8 is a plot showing the tumor cell growth inhibition by selected concentrations of 7β-hydroxycholesterol in K-562 cell culture fluid: ⅒ (0.4 mg/mL culture fluid; 0.9% ethanol present in culture), ⅛₀ (0.03 mg/mL culture fluid; 0.10% ethanol present), and ⅟₃₂₀ (0.007 mg/mL culture fluid; 0.030% ethanol present).

In a preferred aspect, the invention comprises the novel pyranoside compounds having the above formulas. The novel 7β-hydroxycholesterol DDH pyranoside in particular and its 7-keto precursor possess valuable pharmacological properties. These compounds are equivalent in this respect to the related aglycon 7β-hydroxycholesterol (7β-OHC) as the bishemisuccinate colamine salt which at low parenteral dosage has been shown in clinical studies to selectively inhibit the proliferative phase growth of cancer cells without substantial side effects, as reported in "Clinical Studies" by Dr. Steinkellner, Ortho Moleculair, No. 5 (1989) pp. 206–11, incorporated herewith by reference. The mentioned 7β-OHC salt also exhibits normalizing effects such as a drive-enhancing (stimulating) activity as well as a tranquilizing activity. The present aglycon or steroidal moiety, which is 7β-hydroxycholesterol also known as 5-cholestene-3β,7β-diol, and its 7-keto analog of the present invention are endogenous steroids of the thymus gland, being native signal substances of the cellular immune response. The aglycon compound 7β-hydroxycholesterol previously has been successfully employed as indicated in the treatment (free of side effects) of cancer diseases of several phenotypes. For example, a preferred parenteral dosage regimen in treating the proliferative phase growth of the kind described, allowing for ethical considerations and practices exercised in the clinician's judgment, calls for administration of about 10 to about 40 mg of 7β-OHC DDH pyranoside per 70 Kg of body weight, once a day or less often while analysis is made of tumor markers such as CEA, TPA, etc. so that the dosage can be adjusted from time to time to normalize the tumor marker level. While the alpha-isomer, 5-cholestene-3β,7β-diol, is formed in the liver as the first degradation product of cholesterol and possesses no physiological activity, the beta-isomer, 5-cholestene-3β,7β-diol (as well as its 7-keto analog), is formed in the thymus gland of all mammals as a universal signal substance of the mammalian immune defense. It owes its activity, which is solely directed to malignant cell surfaces, to the fact that it is bound unspecifically by LDL (low density lipoproteins). The lipoproteins serve both for the essential transport of cholesterol into the interior of the cell and for the construction of the cell membranes. The beta-isomer also owes its activity to the fact that it is transferred by the lipoproteins, presumably via the NK-cells (natural killer cells) onto the cell membranes of deviated tissue, particularly onto cancerous tissue. As the receptors of LDL on the surface of cancer cells are degeneratively modified, having undergone a modification of their spatial structure in contrast to normal soma cells, the 7β-hydroxycholesterol effects a blocking of the receptors modified in this way. This is analogous to the plugging of a bottle, wherein the cancer cell is cut off from the supply of the vital cholesterol. Hence, it follows that an osmotic excess pressure builds up in the interior of the cancer cell, finally leading to the colloid-osmotic induced rupture of the cancer cell. The cytoplasma of the cancer cell is then forced out. Thus, the cancer cell ceases to exist (FIG. 8).

The cytolytic event, lasting only for about 8 to 10 minutes, has been investigated microscopically and recorded by Alex Matter [Microcinematographic and electron microscope analysis of target cell lysis induced by cytotoxic T lymphocytes, Immunology 36, 179–190 (1979)]. No statement concerning the chemical nature of the body's own active substance is made.

In 1976, 7β-hydroxycholesterol was detected, together with progesterone, 11β-hydroxyprogesterone, cortexone and 7-ketocholesterol, in thymus extracts for the first time by Klemke (unpublished results), using the antimony trichloride reaction for sterols, IR-spectroscopy and NMR-spectroscopy. Reisch and El Shakary, Scientia Pharmaceutica 50, 75–78 (1982) confirmed these findings after the group of J. P. Beck in Strasbourg, J. Chem. Res. (S) 1977, 217–219, had previously found that 7β-hydroxycholesterol constitutes the antiproliferatory-active substance of a very ancient Chinese drug, the Bombyx cum Botryte, a silkworm (Bombyx mori) having been killed by a microscopic fungus (Botrytis bassiana Balls). Further details have been published in Vol. 32/TUMOSTERON "Schriftenreihe Krebsgeschehen" of the Verlag fur Medizin, Heidelberg 1986. The 5-cholestene-3β,7β-diol (i.e., 7β-hydroxycholesterol, 7β-OHC) was recognized as a biochemical signal compound of the body's own immune defense system. In contrast to the conventional poorly selective cytotoxic treatment of disease conditions involving normal body cells and cancer cells, 7β-OHC turns out to be effective at substantially non-toxic dosage and capable of eliminating cancer cells of representative phenotypes while not affecting healthy cells.

A glycosylated cholesterol is known from Chemical Abstracts Vol. 97, 1982 6734s, which possibly might constitute a neoplastic inhibitor. However this molecule has in its glycosidic moiety at $C_2$ a bulky 2-chloroethyl-aminocarboxamido group and the 7β-hydroxy group is lacking. This latter group, however, is sterically important according to the present invention, for its contribution to in vivo conformation with the respective onco-cellular receptor.

Also known are the 7-hydroxy- and 7-ketocholesterols which are described, respectively, as being useful as an immunoregulatory or antiphlogistic agent (U.S. Pat. No. 4,157,391, incorporated herewith by reference). Water-soluble cholesterol salts, useful as standards for the determination of cholesterol in biological fluids, are also known from U.S. Pat. No. 3,859,047. These are the morpholine, the cyclohexylamine, and the tris (hydroxymethyl) aminomethane salts of cholesteryl hemisuccinate.

The novel steroid and non-steroid compounds of the invention can be used in the form of pharmaceutical preparations comprising each such compound in a pharmacogically effective amount in admixture with a pharmaceutically acceptable carrier which may be conventional per se. These preparations may be formulated by well known procedures. In these respects, see for example Remington's Pharmaceutical Sciences, Chapter 43, 14th Ed., Mack Publishing Co., Easton, Pa. 18042, USA. These preparations can be administered in any suitable way such as orally, e.g. in the form of tablets, dragees, gelatin capsules, soft capsules, solutions, emulsions or suspensions or parenterally, e.g., in the form of injectable solutions at suitable pH, e.g., ca. 7.5, or topically, e.g., in the form of a cream.

The carriers mentioned above may constitute pharmaceutically inert inorganic or organic materials. Examples of carriers for tablets, capsules and hard gelatine capsules include lactose, maize-starch or derivatives thereof, talcum, stearic acid or salts thereof. Examples of carrier for soft gelatine capsules include vegetable oils, waxes, fats, semisolid and liquid polyols. Examples of carriers for the manufacture of solutions or syrups include water, ethanol, propylene glycol, saccharose, invert sugar and glucose. Examples of carriers for injectable solutions include water, ethanol, polyols, propylene glycol, glycerol, and vegetable oils. The pharmaceutical preparations may also comprise conventional pharmaceutical adjuvants such as preservatives, solubilizers, stabilizers, humectants, emulsifiers, sweetening agents, dyes or scents, salts (e.g., to modify the osmotic pressure), buffers, coating agents or antioxidants. They may also comprise at least one other systemically biocompatible and therapeutically valuable ingredient in a biochemically effective amount, including an antioxidant such as tocoquinones (tocopherols), glutathione, cysteine, ascorbic acid sodium salt, methionine, and the like.

The pharmaceutical preparations may be manufactured by admixing the compound according to this invention, if desired in combination with other therapeutically valuable substances, with an acceptable pharmaceutical carrier and, if desired, with a pharmaceutical adjuvant, and transforming the admixture into the desired form for administration.

The invention and the best mode for practicing the same are illustrated by the following examples.

EXAMPLE 1

Preparation of Cholesteryl 4,6-Di-O-acetyl-2,3-dideoxy-α-D-erythro-hex-2-enopyranoside

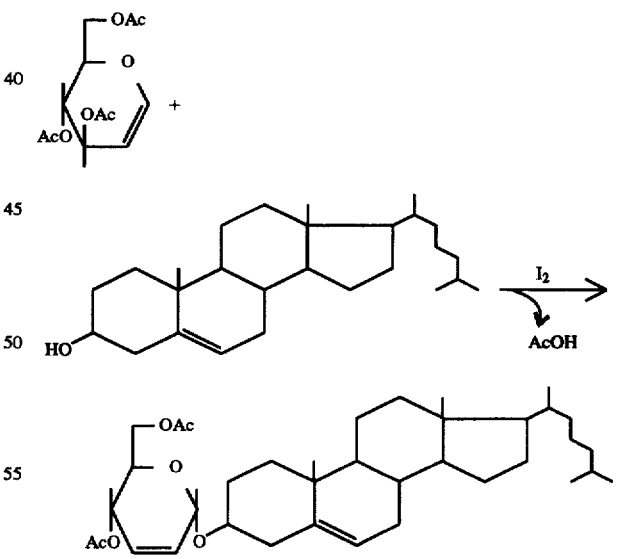

Iodine (5.00 g, 0.02 mole) was dissolved with stirring in 300 mL of benzene in a 2-liter three-necked flask fitted with stirrer, reflux condenser and thermometer. To this wine-red solution were added a solution of 27.2 g (=0.10 mole) of 3,4,6-tri-O-acetyl-D-glucal and 38.6 g (=0.10 mole) of cholesterol (5-cholesten-3β-ol) in 700 ml of benzene. In the course of 2 hours the mixture was heated to 70°–75° C. The reaction was monitored by IR-spectroscopy; it was terminated only when the peak of the glucal at 1650 cm$^{-1}$ (FIG. 1) had disappeared. After removal of the flask heater, the reaction solution was rapidly cooled in a water-bath to about 20°–30° C. After transfer into a 2-liter separatory funnel the cooled wine-red reaction solution was thoroughly shaken until complete discoloration with 10% aqueous $Na_2S_2O_3$, washed twice with water, treated with activated carbon, dried over anhydrous $Na_2SO_4$ and the solvent distilled off, finally in vacuo.

Crude yield: 58.3 g (97.%)

The product, cholesteryl 4,6-di-O-acetyl-2,3-dideoxy-α-D-erythro-hex-2-enopyranoside, was recrystallized from 2 liters of $CH_3OH$.

Figure 2:
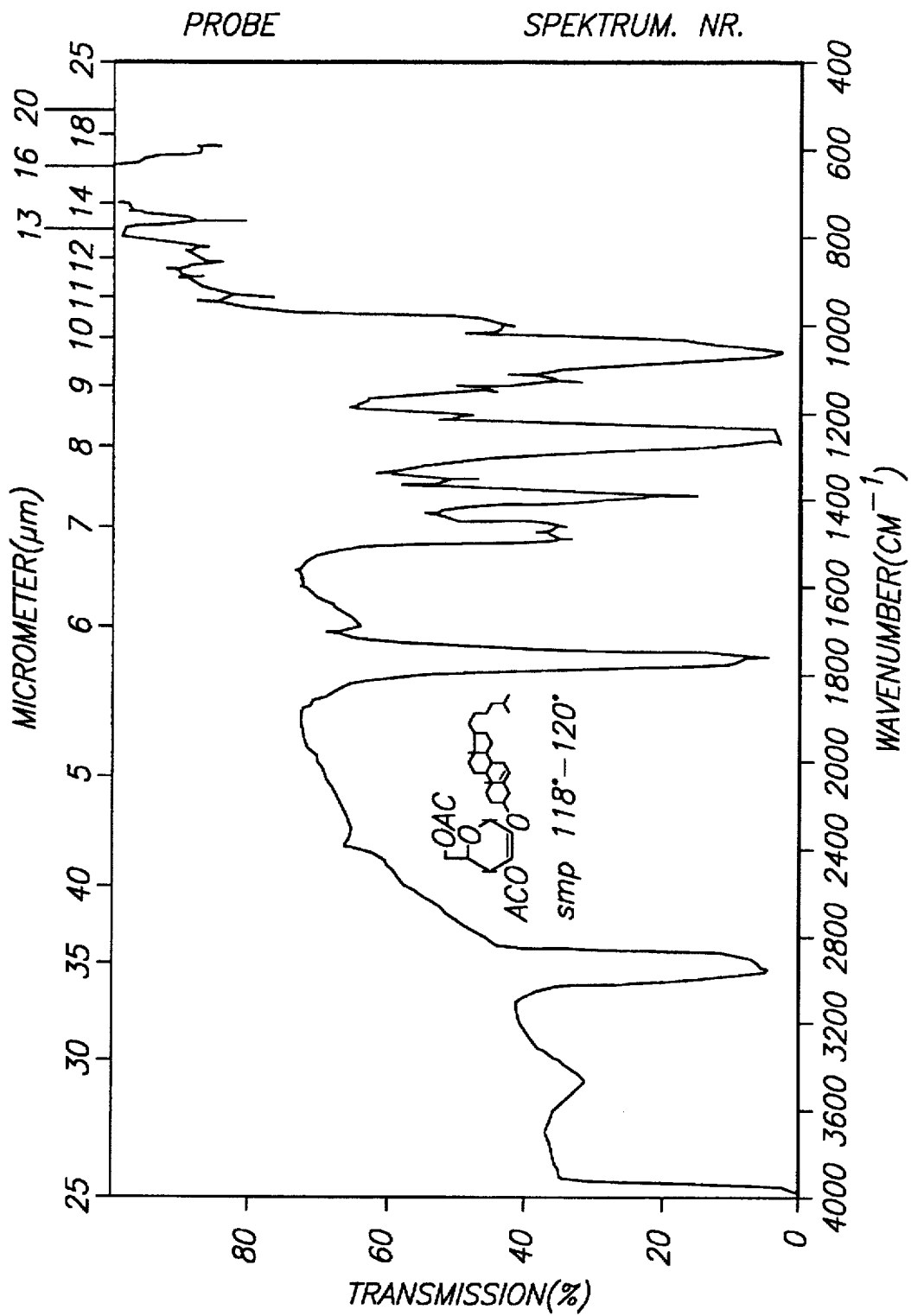
FIG. 2 is an infrared spectrum of the glycosylation product of Example 1.
Figure 3:
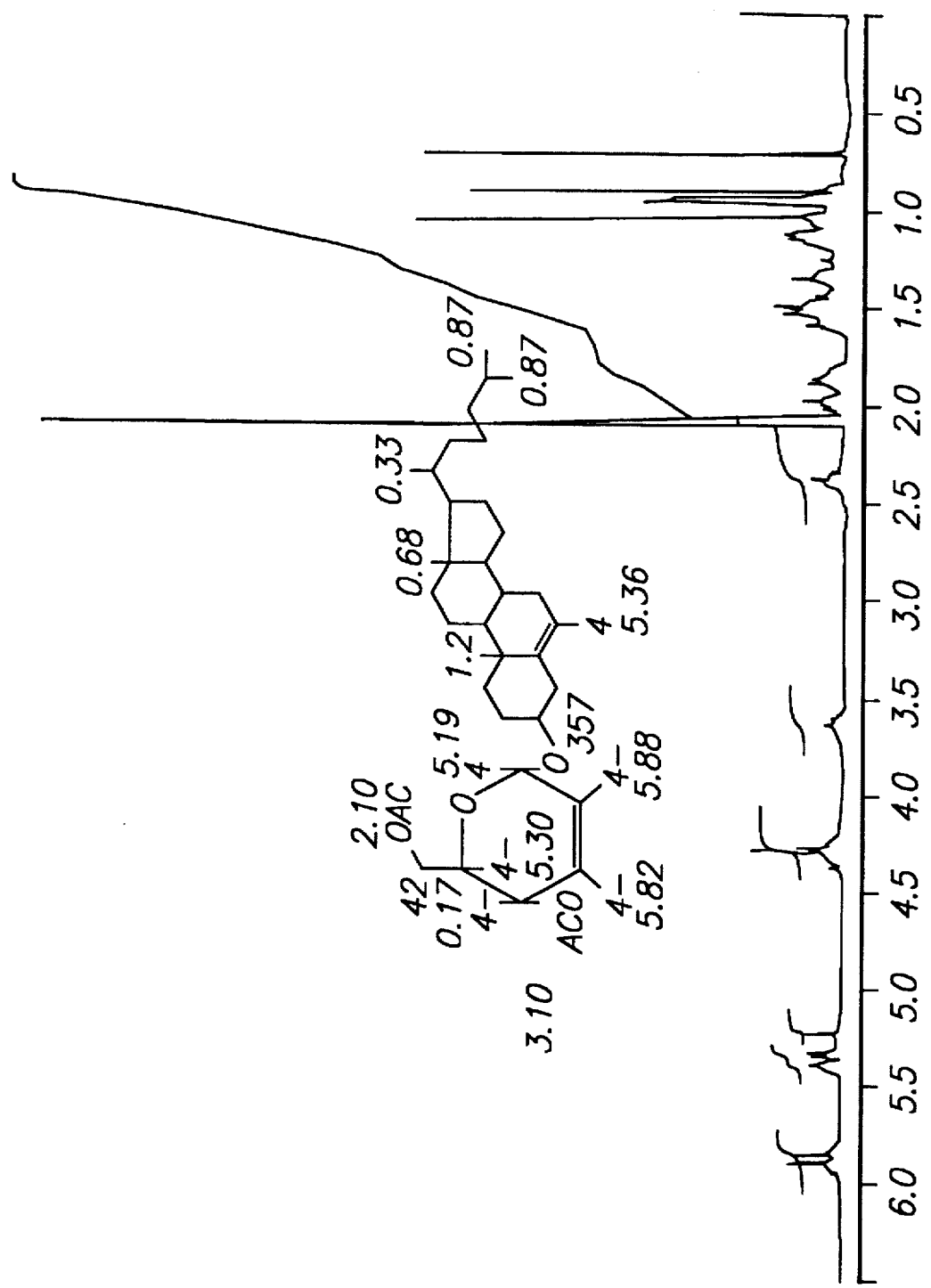
FIG. 3 is an NMR spectrum of the same glycosylation product of Example 1.

Yield: 57.0 g (95.1%)
Mp: 118°–120° C.
IR-spectrum: FIG. 2
NMR-spectrum: FIG. 3

EXAMPLE 2

Preparation of 7-ketocholesteryl 4,6-Di-O-acetyl-2,3-dideoxy-a-D-erythro-hex-2-enopyranoside

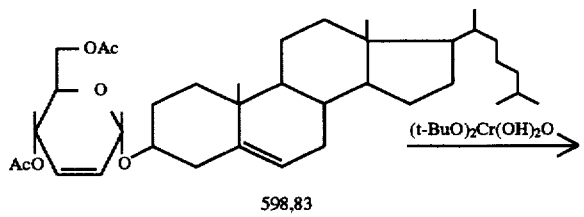

598,83

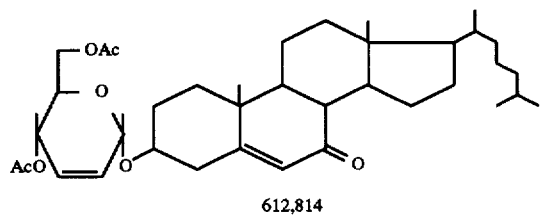

612,814

In a 250-mL three-necked flask fitted with reflux condensor, dropping funnel, thermometer and magnetic stirrer, 6.00 g (=0.01 mole) of the unsaturated glycoside title product from Example 1 of mp 118°–120° C. was dissolved in 45 mL of $CCl_4$ and the resulting solution was heated to reflux (80° C.). In the course of 30 minutes a mixture of 10 mL of $Ac_2O$ (acetic anhydride) and 40 mL of a t-butyl chromate solution, prepared according to the procedure given in the appendix, was added dropwise to the boiling solution and stirred for another 10 hours at the boiling point. After cooling, a solution of 6.0 g of oxalic acid in 60 mL of water was added dropwise in the course of 45 minutes at 5° C. to 10° C. in an ice-bath followed by 4.2 g of solid oxalic acid. Stirring was then continued for another 2 hours. Thereafter separation took place in the separating funnel, the upper dark aqueous phase being extracted twice with $CCl_4$, the combined $CCl_4$-solutions extracted with water, saturated solution of $NaHCO_3$ and then with water again, in this order, and dried over $Na_2SO_4$. Finally the solution was decolorized with activated carbon. After concentration in vacuo, the straw-yellow residue was dissolved in 25 mL of a mixture consisting of cyclohexane 40: ethyl acetate 10: chloroform 1 and chromatographed on a silica gel column (diameter 2.5 cm; height 25 cm), charged with 60 g of silica gel 40 (Merck Article 10180) and the same solvent mixture.

Yield: Fraction 1: 1.8 g (30%) of unchanged starting material.

Figure 4:
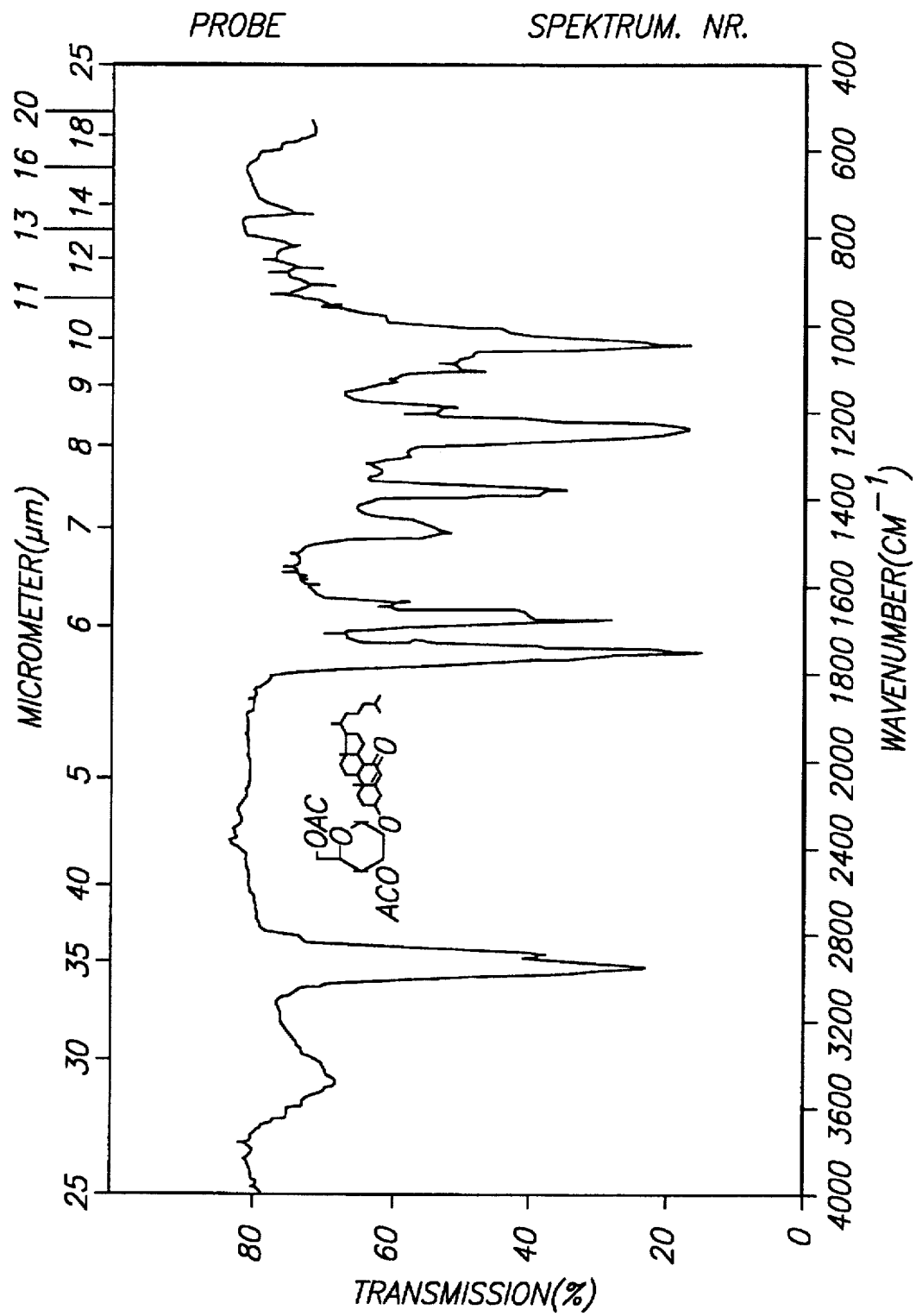
FIGS. 4 and 5 are the IR-spectrum and the NMR-spectrum, respectively, of the ketone product of Example 2.
Figure 5:
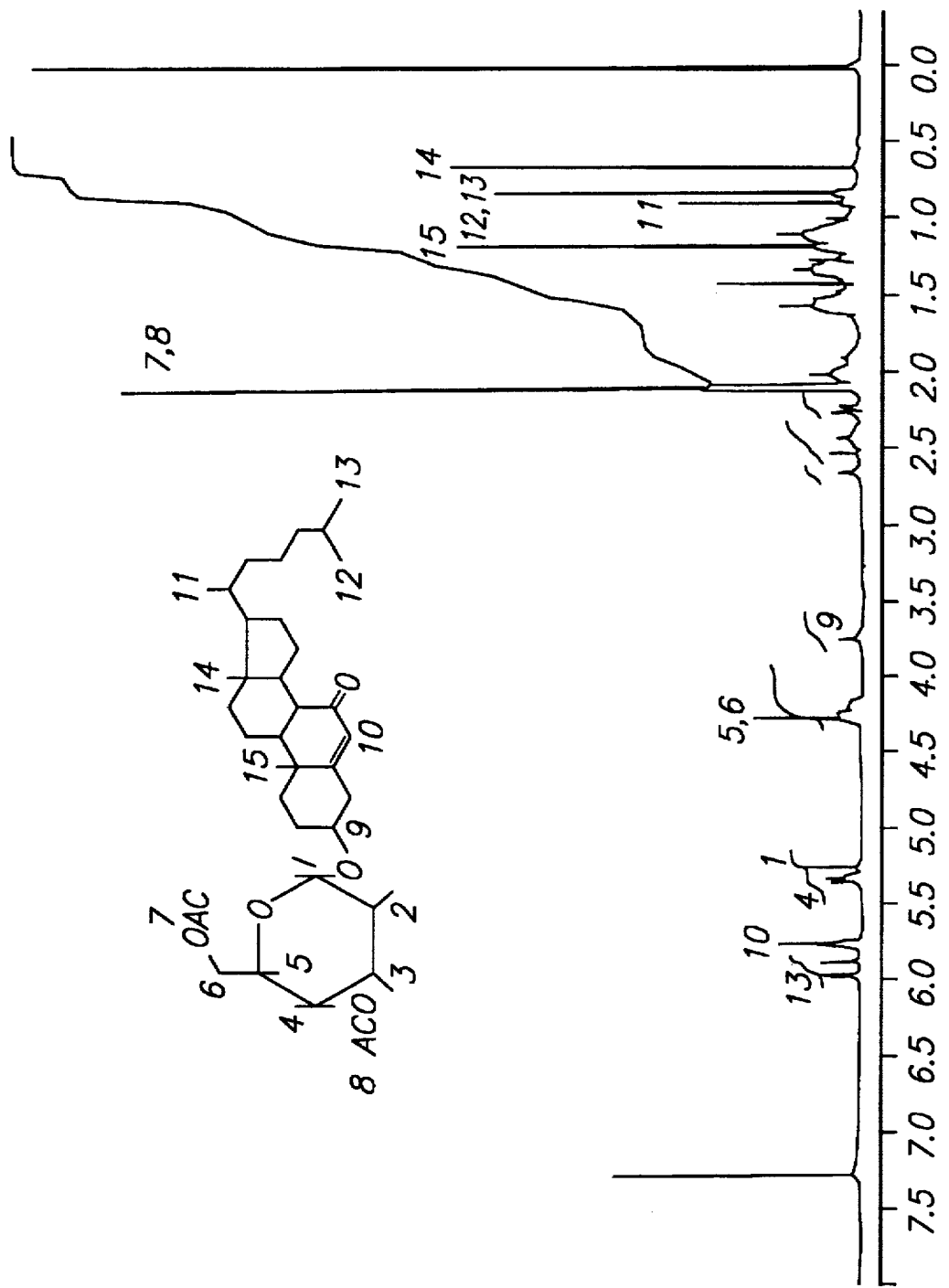

Fraction: 2: 4.20 g (69%) of 7-keto-compound
Mp: 113°–115° C.
IR-spectrum: FIG. 4
NMR-spectrum: FIG. 5

Appendix

Preparation of t-butyl chromate

A 500 mL beaker was charged with 187.2 g (2.5 mole) of t-butylalcohol of mp 24.5° C. and the t-butylalcohol was warmed to 28° C. upon which time it melted. To this solvent, 74 g (=0.74 mole) of $CrO_3$ was added with stirring. In order to keep the mixture temperature below 30° C., occasional cooling with ice-water was necessary. The liquid product thus formed was diluted in a separatory funnel with 520 mL of $CCl_4$ and the mixture was left to stand overnight. This standing is important to allow clarification of the solution. The upper dark layer was then separated. The clear $CCl_4$-solution was dried over 50 g of anhydrous $Na_2SO_4$. The $Na_2SO_4$ was removed by filtration and the $Na_2SO_4$ was washed with 320 mL of $CCl_4$. Thereafter, the combined $CCl_4$-solutions were concentrated to 400 mL in vacuo in a water-bath at a temperature of 40° C. to 45° C., wherein excess t-butylalcohol and $CCl_4$ were both distilled azeotropically. The solution thus obtained is relatively stable for storage as it may be kept unchanged in the refrigerator at −1° C. for at least one month.

EXAMPLE 3

Preparation of 7-β-Hydroxycholesteryl 2,3-Dideoxy-α-D-erythro-hex-2-enopyranoside

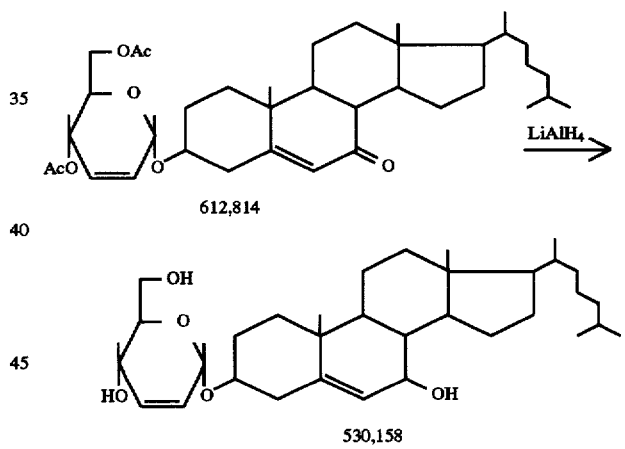

The pure ketone product compound from Example 2 (6.13 g, 0.10 mole) with mp 113°–115° C. was dissolved by heating in 100 mL of peroxide-free ether which had been distilled over metallic sodium and cooled to room temperature. A solution of 0.8–1.0 g (=0.021 mole) $LiAlH_4$ in 100 mL of absolute ether was added to a 500 mL three-necked flask with magnetic stirrer, reflux condensor and thermometer. The ethereal solution of the aceto-7-keto-glucoside was then added dropwise with sufficient stirring to assure that the reaction temperature did not substantially exceed 20° C. After addition had been completed, which may take up to two hours, stirring was continued for another two hours at room temperature.

The reaction mixture was cooled in ice-water and treated drop by drop with $H_2O$ until all $H_2$ (conducted to the outlet of the hood by means of a tube) had evolved. $H_2O$-consumption was about 5.0 mL. On a larger scale, the use of $CH_3COOC_2H_5$ is recommended. In order to dissolve the inorganic salts formed, the mixture was stirred with 16 mL of 10% aqueous $H_2SO_4$ and, after transfer to a 500-mL separating funnel, diluted with 100 mL of ether and shaken thoroughly. Thereby, the reaction product, comprising a mixture of the title 7β-OH compound and its 7β-OH isomer, which had precipitated out, goes completely into solution. The separated acidic aqueous solution was extracted once with ether and the combined ethereal solution was washed with 100 mL of brine in two portions of 50 ml each. After drying over anhydrous $Na_2SO_4$, the filtrate was kept in the refrigerator at −1° C. for nine hours. The crystals thus obtained were collected by suction filtration ($G_4$ filter) and weighed.

Crude yield: 5.10 g (96% of theory)
Mp: 165°–167° C.

The product comprising a mixture of the title 7β-OH compound and its 7α-OH isomer was dissolved in 25 mL of dioxane (or THF) by heating and the resulting solution was chromatographed on a column of silica gel (diameter 5.0 cm; height 70 cm) charged with 300 g of silica gel 40 (Merck Article 10180) using a solvent mixture consisting of dichloromethane 1: acetone 1.

Yield

Fraction 1: 0.35 g (6.8%) of 7α-OH-compound, mp: 159°–161° C.

Fraction 2: 4.60 g (90%) of 7β-OH-compound, mp: 181°–183° C.

Figure 6:
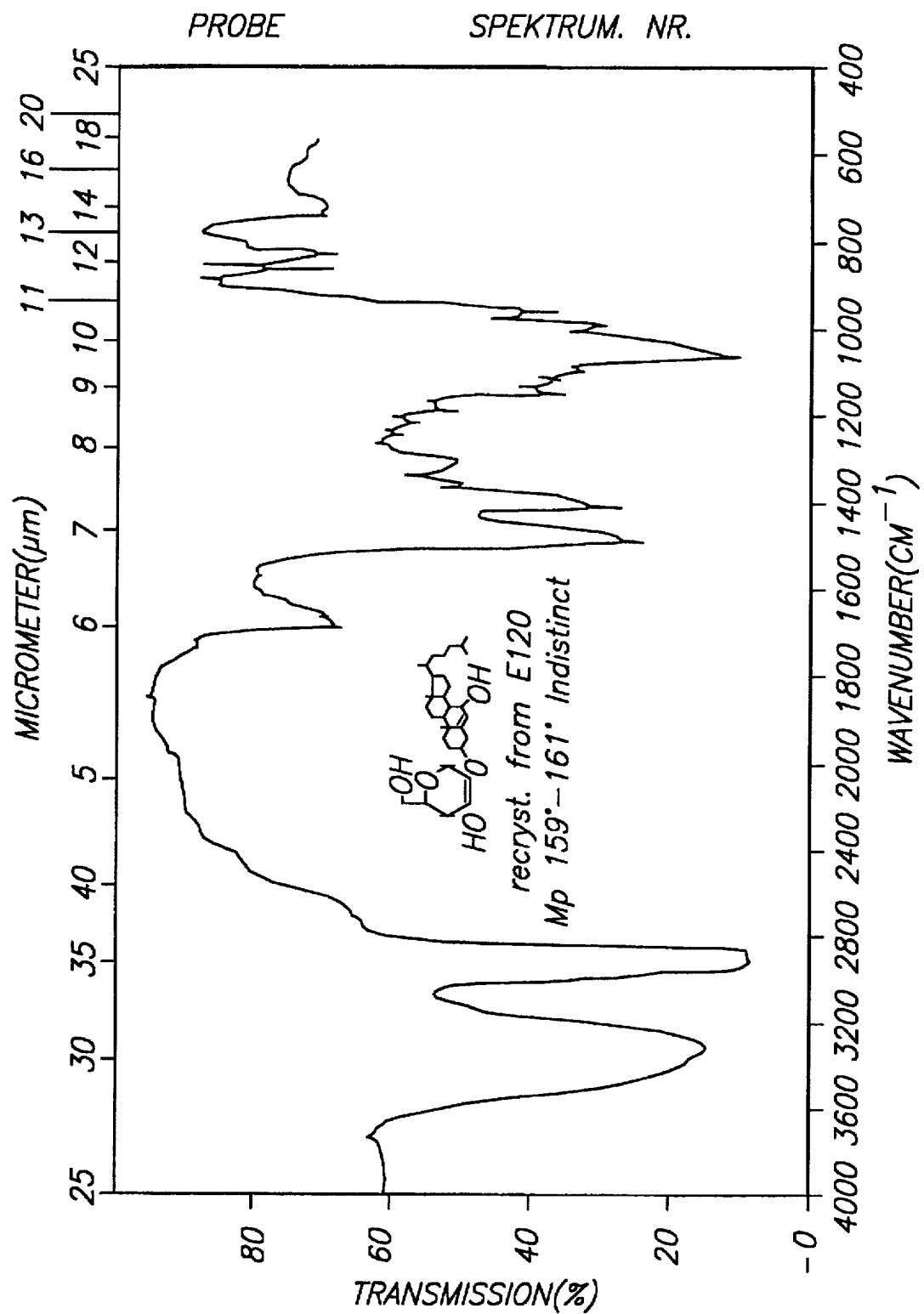
FIGS. 6 and 7 are the IR-spectrum and the NMR-spectrum, respectively, of the 7β-OHC product of Example 3.
Figure 7:
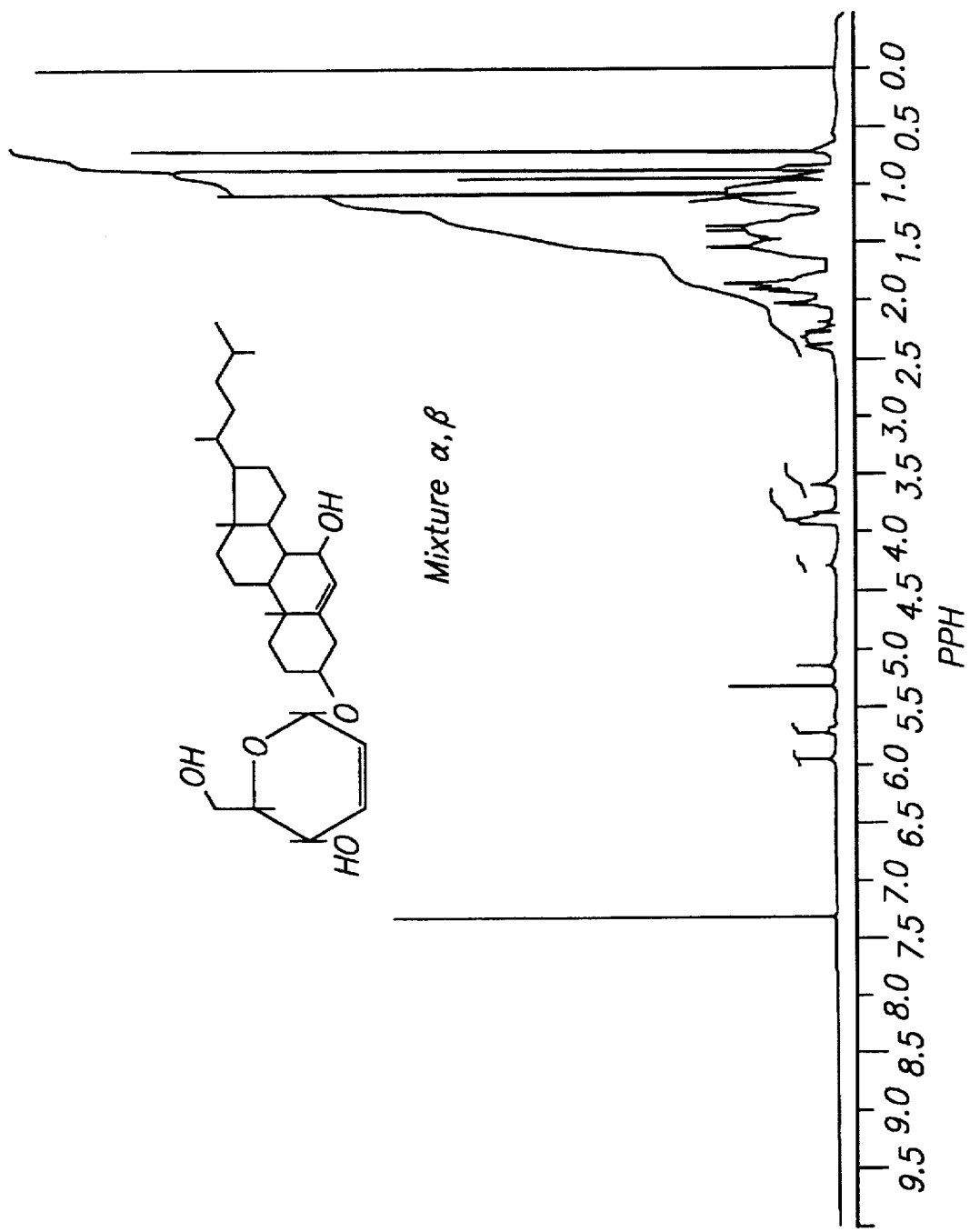

IR-spectrum: FIG. 6
NMR-spectrum: FIG. 7

EXAMPLE 4

| Tablet | |
|---|---|
| 7β-Hydroxycholesteryl 2,3-dideoxy-α-D-erythro-hex-2-enopyranoside | 200 g |
| Niacine amide | 600 g |
| Thiamine, HCl | 300 g |
| Pyridoxal phosphate | 200 g |
| Pyridoxal palmitate | 400 g |
| Magnesium citrate | 300 g |
| Magnesium stearate | 200 g |
| Milk sugar or corn starch | 400 g |

Combine the mixture in a planetary mixer and mix for 3 minutes. The mixture is milled and the total blend is drum rolled for 5 minutes. Compressed tablets of 260 mg of the total mix are formed with appropriate size punches, each tablet containing 20 mg of the cholesteryl glycoside for oral administration.

EXAMPLE 5

| Suppository | | |
|---|---|---|
| a. | 7β-Hydroxycholesteryl 2,3-dideoxy-α-D-erythro-hex-2-enopyranoside | 0.1 g |
| b. | Milk sugar | 1.0 g |
| c. | Aerosil | 0.2 g |
| d. | Suppository base, PEG (Stadinol) | 23.7 g |
| | | 25.0 g |

Melt the polyethylene glycol and mix ingredients a, b and c into the melt. Mold this total into appropriate suppositories. For adults, the mixture makes for 10 suppositories.

EXAMPLE 6

| Capsule | | |
|---|---|---|
| a. | 7β-Hydroxycholesteryl 2,3-dideoxy-α-D-erythro-hex-2-enopyranoside | 5 mg |
| b. | Glutathione | 100 mg |
| c. | L-Cysteine | 30 mg |
| d. | Vitamin C | 200 mg |
| e. | Milk sugar | 40 mg |
| | | 365 mg |

Capsules of appropriate size are each filled with the mixed and blended ingredients to provide a capsule containing 5 mg of the cholesteryl glycoside.

EXAMPLE 7

| Salve | | |
|---|---|---|
| a. | 7-β-Hydroxycholesteryl 2,3-dideoxy-α-D-erythro-hex-2-enopyranoside | 1.0 g |
| b. | Procaine | 2.0 g |
| c. | Niacin | 5.0 g |
| d. | Ointment Base (Eucerin ®, Beiersdorf) | 92.0 g |
| | | 100.0 g |

Ingredients a), b) and c) are mixed in and blended with the ointment base which is subdivided for topical application of a unit dose of salve containing 10 mg of ingredient a).

EXAMPLE 8

Injectable

7β-Hydroxycholesteryl 2,3-dideoxy-α-D-erythro-hex-2-enopyranoside (1.0 g) is dissolved in 30 mL of ethanol with warming and stirred with 162 mL of 1,2-propylene glycol. To the resulting clear solution there is added 8 mL of water with mixing, and the solution is filtered and placed in ampoules and sealed. This provides 100 ampoules each containing 2 mL of injectable which in turn contains 10 mg of the active 7β-hydroxycholesteryl glycoside.

EXAMPLE 9 p-Acetoamidophenyl 6-O-acetyl-4-O-(2,3,4,6-tetra-O-acetyl-α-D-glucopyranosyl)-2,3-dideoxy-α-D-erythro-hex-2-enopyranoside (1)

To a solution of 124 mg of 4-acetamidophenyl (Tylenol®) (0.821 mmol) and 520 mg of hexaacetyl D-maltal (0.930 mmol) in 14 mL of dry THF was added 47 mg of iodine (20 mol %) at room temperature. The mixture was refluxed for 12 hours, upon which time the solution was cooled at room temperature and diluted with 40 mL of chloroform. The resulting mixture was washed first with 0.1M aqueous $Na_2S_2O_3$ (30 mL) and then with 10% aqueous $NaHCO_3$ (30 mL). The organic layer was dried over anhydrous MgSO$_4$ and the solvent was removed by rotary evaporation. The resulting solid residue was purified by silica gel flash column chromatography using 9:1 dichloromethane/MeOH as the eluent, providing 164 mg of a 8:1 α/β anomeric mixture of the acetylated glycoside product 1 (30%) as a light yellow powder: mp 89°–92° C.; R$_f$ 0.50 (9:1 dichloromethane/MeOH); [α]$_D^{22}$+204.5° (c=0.761, MeOH); IR (KBr) 3377 (br,w), 3373 (br,w), 2961 (br,w), 1748 (s), 1672 (m), 1510 (m), 1436 (m), 1369 (m), 1226 (br,s), 1039 (s), 602 (w) cm$^{-1}$.

p-Acetoamidophenyl 4-O-(α-D-glucopyranosyl)-2,3-dideoxy-α-D-erythro-hex-2-enopyranoside (2)

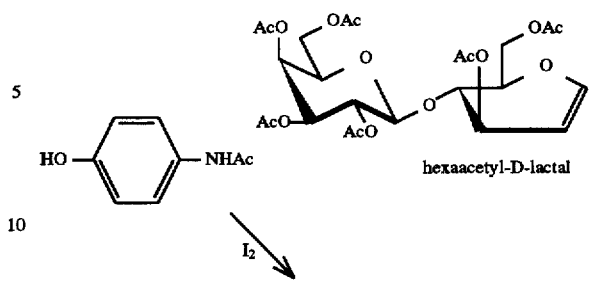

hexaacetyl-D-lactal

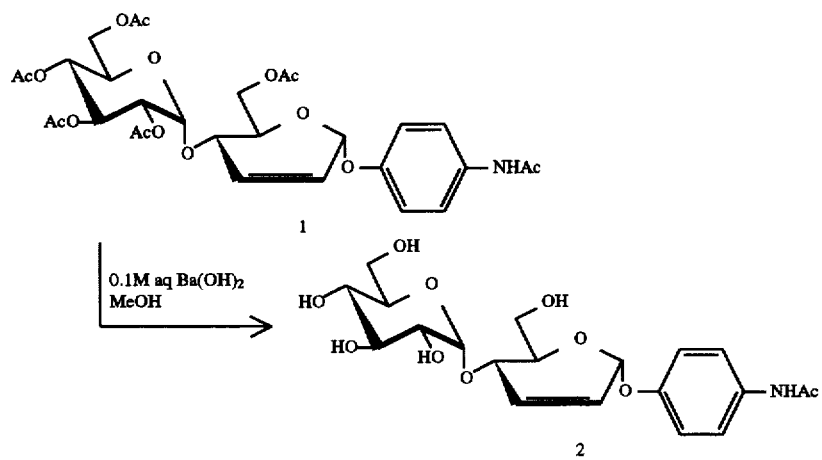

To a solution of 600 mg of pentaacetate 1 (0.910 mmol) in 10 mL of MeOH was added 18 mL of 0.1M aqueous Ba(OH)$_2$ at room temperature. The resulting mixture was stirred at that temperature for 12 hours, upon which time the hydrolyzed product was extracted with 4:1 chloroform/1-butanol (3×50 mL). The combined organic layers were dried over anhydrous MgSO$_4$ and the solvent was removed by rotary evaporation. The crude solid residue thus obtained was purified by silica gel flash column chromatography using the ethyl acetate to MeOH gradient as the eluent, providing 160 mg of a 8:1 α/β anomeric mixture of the hydrolyzed glycoside (2) (39%) as a white crystalline solid; mp 130°–133° C. (decomp); R$_f$ 0.18 (4:1 ethyl acetate/MeOH); [α]$_D^{22}$+146.9° (c=1.03, MeOH); IR (KBr) 3400–3250 (br,s), 2978 (w), 1646 (m), 1510 (m), 1405 (m), 1231 (m), 1035 (s), 600 (w) cm$^{-1}$.

EXAMPLE 10 p-Acetoamidophenyl 6-O-Acetyl-4-O-(2,3,4,6-tetra-O-acetyl-β-D-galactopyranosyl)-2,3-dideoxy-α-D-erythro-hex-2-enopyranoside (3)

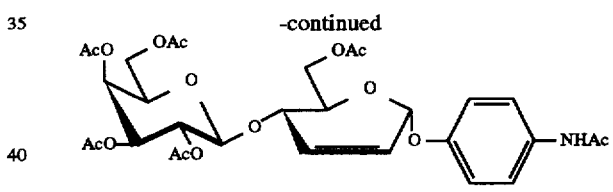

A procedure similar to the one described for the preparation of 1 was employed using 100 mg of 4-acetamidophenol (0.660 mmol), 370 mg of hexaacetyl-D-lactal (0.750 mmol), and 40 mg of iodine (20 mol %). Purification of the crude product by silica gel flash column chromatography using 9:1 dichloromethane/MeOH as the eluent provided 164 mg of a 8:1 α/β-anomeric mixture of the acetylated glycoside product 3 (30%) as a light yellow powder; mp 94°–97° C.; R$_f$ 0.48 (9:1 dichloromethane/MeOH); [α]$_D^{22}$+81.9° (c=1.09, MeOH); IR (KBr) 3474 (w), 2960 (w), 1750 (s), 1690 (m), 1515 (m), 1434 (m), 1371 (s), 1232 (s), 1170 (m), 1135 (m), 1075 (s), 602 (m) cm$^{-1}$.

p-Acetoamidophenyl 4-O-(β-D-galactopyranosyl)-2,3-dideoxy-α-D-erythro-hex-2-enopyranoside (4)

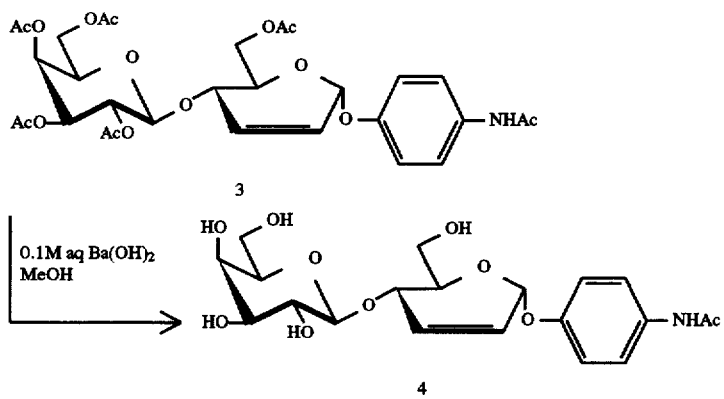

A procedure similar to the one described for the preparation of 2 from 1 was employed using 340 mg of pentaacetate 3 (0.510 mmol), 5 mL of MeOH, and 9 mL of 0.1M Ba(OH)$_2$. Purification of the crude product by silica gel flash column chromatography using the ethyl acetate to MeOH gradient provided 101 mg of a 8:1 α/β-anomeric mixture of the hydrolyzed glycoside product 4 (43%) as a white crystalline solid; mp 155°–159° C. (decomp.); R$_f$ 0.16 (4:1 ethyl acetate/MeOH); [α]$_D^{22}$+101.1° (c=0.942, MeOH); IR (KBr) 3600–3200 (br,s), 2987 (s), 2977 (s), 1662 (m), 1550 (m), 1509 (m), 1413 (m), 1231 (m), 1074 (br,s), 981 (m) cm$^{-1}$.

Solubility Study of Acetaminophen Derivatives

The solubility of the two acetaminophen derivatives (Examples 9 and 10) in 14 mM phosphate buffered saline (PBS) pH 7.4 was determined and compared with the solubility of non-derivatized acetaminophen. It was determined that the two acetaminophen derivatives had much greater solubility than that of the non-derivatized acetaminophen. All work was performed at 23° C.

Method

The solubility of both derivatives was determined by continual addition, with agitation, of the derivatives to a known amount of buffer. When a significant precipitate was observed, the respective solutions were centrifuged and the optical density at 250 nm of the resulting clear supernatant was determined. From the optical density of the supernatant, the concentration was obtained by comparison with non-derivatized acetaminophen standard curves.

Results

The following maximum solubility of acetaminophen was observed

In 14 mM PBS pH 7.4 7.0 mg/ml

The following maximum solubility of the Example 9 glycoside was observed

In 14 mM PBS pH 7.4 60 mg/ml

The following maximum solubility of the Example 10 glycoside was observed

In 14 mM PBS pH 7.4 55 mg/ml

The results of this comparison show that each derivative has a significantly greater solubility, in the buffer tested, than non-derivatized acetaminophen. Each derivative has a solubility approximately 8 times greater in 14 mM PBS pH 7.4 than observed with non-derivatized acetaminophen.

The above glycosylation reaction carried out in benzene at 70° C. is selective for the desired alpha isomer rather than the beta isomer. Thus the reaction typically produces a ratio of alpha to beta cholesteryl glycoside anomers (α:β) of greater than 20:1. Similarly, in THF at 67° C. and at room temperature the reaction in either case typically produces an α:β anomer ratio of about 9:1.

The invention comprises not only the above glycoside products but also other glycoside products made by the above procedure using as starting materials equivalent amounts of the glucal (or other suitable glucal) and the aglycon selected for glycosidation. Suitable aglycon compounds are selected (for their known use as aglycons) from the aforementioned aliphatic, alicyclic, aliphatic-aromatic or aromatic compounds having a primary, secondary or tertiary functional group preferably selected from —OH, —SH, and —COOH. Especially preferred glycoside products made by the above procedure are the respective 4,6-di-O-acyl or acetyl-2,3-dideoxy-α-D-erythro-hex-2-eno-pyranosides of the following aglycon compounds which as DDH pyranoside products are characterized by known IR and NMR spectroscopy data available from the referenced literature.

| Hydroxy Aglycon | The Merck Index XI Monograph No. | Use |
| --- | --- | --- |
| Cholic acid | 2206 | choleretic |
| Clavulanic acid | 2342 | antibacterial |
| Amoxicillin | 610 | antibacterial |
| Daunorubicin | 2825 | antineoplastic |
| Lovastatin | 5460 | antihyper cholesterolemic |
| Mevastatin | 6088 | antihyper cholesteroiemic |
| Simvastatin | 8491 | antihyperlipidemic |

A general procedure was used in which, instead of cholesterol, a starting material (i.e., a substrate) having at least one functional group (e.g., OH, SH, and/or —COOH) was used. The procedure is detailed as follows:

GENERAL PROCEDURE

The substrate (1 equiv) was added to a stirring solution of glucal (0.5–1.0 g) and iodine (20 mol %) in THF at room temperature. The reaction was monitored by thin-layer chromatography. Reaction times are listed for each compound. Upon completion the solution was diluted with ether and washed with 10% aqueous Na$_2$S$_2$O$_3$ solution. The layers were separated and the aqueous layer was extracted with additional ether. The combined organic layers were dried over Na$_2$SO$_4$, concentrated, and purified by column chromatography on 230–400 mesh SiO$_2$. All products were recovered as viscous oils except for those compounds for which a melting point is given.

Note

The thiols were added at lower temperatures as indicated for each adduct.

| ILLUSTRATIVE SUBSTRATES | |
|---|---|
| ALCOHOLS (all over 90% yield; α-anomer:β-anomer = 5–8:1) | |
| methanol | |
| ethanol | |
| isopropanol | |
| tert-butyl alcohol | |
| benzyl alcohol | |
| allyl alcohol | |
| PHENOLS (α-anomer:β-anomer = 6–8:1) | |
| phenol (70%) | |
| p-methoxyphenol (ca. 65%) | |
| p-nitrophenol (ca. 60%) | |
| THIOLS (highly reactive) | |
| ethyl mercaptan | α-anomer:β-anomer = 16:1 |
| (−78° C. to −55° C.) (35%) | |
| isopropyl mercaptan | α-anomer:β-anomer = 15:1 |
| (−78° C. to 0° C.) (77%) | |
| tert-butyl mercaptan | α-anomer only |
| (−25° C.) (68%) | |
| thiophenol | α-anomer:β-anomer = 20:1 |
| (room temperature) (50%) | |
| CARBOXYLIC ACID | |
| acetic acid | α-anomer:β-anomer = 10:1 |
| (catalytic) (80%) | |

SPECTROSCOPIC DATA FOR ALCOHOL (ROH) PHENOL (ArOH) AND CARBOXYLIC (RCOOH) ADDUCTS

R=Me (Reaction Time=30 min. Yield=87%)

$^1$H NMR (CDCl$_3$; 300 MHz) δ2.087 (s,3H), 2.111 (s,3H), 3.457 (s,3H), 4.05–4.13 (m,1H), 4.188 (1H) and 4.266 (1H) (ABq,J$_{AB}$=12.1 Hz; the 4.188 peaks are further split into d with J=2.5 Hz; the 4.266 peaks are further broken down into d with J=5.3 Hz), 4.934 (s,1H), 5.322 (dd,1H,J=9.7, 1.4 Hz), 5.834 (1H) and 5.894 ppm (1H) (ABq,J$_{AB}$=10.6 Hz; the 5.834 peaks are further split into dd with J=2.0, 2.0 Hz).

$^{13}$C NMR (CDCl$_3$; 75.5 MHz) δ20.56, 55.70, 63.26, 65.75, 67.35, 95.60, 128.15, 129.38, 170.08, 170.36 ppm.

IR (KBr) 2956, 2939, 2910, 1744, 1456, 1449, 1438, 1372, 1233, 1188, 1148, 1137, 1107, 1072, 1048 cm$^{-1}$.

R=Et (Reaction Time=50 min. Yield=97%) mp (hexanes=76°–77.5° C.

$^1$H NMR (CDCl$_3$; 300 MHz) δ1.256 (d,J=7.1 Hz,3H), 2.084 (s,3H), 2.105 (s,3H), 3.584 (1H) and 3.837 (1H) (ABq, J$_{AB}$=9.7 Hz; both sets of peaks are further split into q with J=7.1 Hz), 4.09–4.14 (m,1H), 4.174 (1H) and 4.261 (1H) (ABq, J$_{AB}$=12.2 Hz; the 4.174 peaks are further split into dd with J=2.8, 2.8 Hz; the 4.261 peaks are further split into d with J=5.3 Hz), 5.050 (s,1H), 5.319 (dd,J=9.6,1.4 Hz, 1H), 5.837 (1H) and 5.891 ppm (1H) (ABq, J$_{AB}$=10.2 Hz; the 5.837 peaks are further split into dd with J=1.7, 1.4 Hz).

$^{13}$C NMR (CDCl$_3$; 75.5 MHz) δ15.31, 20.66, 20.83, 63.30, 64.25, 65.75, 67.25, 94.40, 128.37, 129.13, 170.17, 170.53 ppm.

IR (KBr) 2980, 2902, 1738, 1382, 1372, 1274, 1257, 1239, 1229, 1189, 1137, 1133, 1120, 1108, 1084, 1052, 1019 cm$^{-1}$.

R=i-Pr (Reaction Time=65 min. Yield=96%)

$^1$H NMR (CDCl$_3$; 300 MHz) δ1.186 (d,J=6.2 Hz,3H), 1.258 (d,J=6.2 Hz,3H), 2.081 (s,3H), 2.096 (s,3H), 3.988 (dq,J=6.2, 6.2 Hz,1H), 4.12–4.28 (m,3H), 5.133 (s,1H), 5.301 (dd,J=9.5, 1.4 Hz,1H), 5.804 (1H) and 5.875 ppm (1H) (ABq, J$_{AB}$=10.3 Hz; the 5.804 peaks are further split into dd with J=2.6, 2.5 Hz,1H).

$^{13}$C NMR (CDCl$_3$; 75.5 MHz) δ20.59, 20.83, 22.06, 23.54, 63.42, 65.87, 67.22, 70.83, 93.06, 128.82, 128.91, 170.18, 170.55 ppm.

IR (KBr) 2973, 2933, 1744, 1457, 1372, 1231, 1185, 1125, 1101, 1035 cm$^{-1}$.

R=t-Bu (Reaction Time=2 hr. Yield=74%)

$^1$H NMR (CDCl$_3$; 300 MHz) δ1.292 (s,9H), 2.075 9s,3H), 2.085 (s,3H), 4.12–4.28 (m,3H), 5.271 (d,1H,J=8.0 Hz), 5.321 (dd,1H,J=1.3, 1.3 Hz), 5.744 (1H), and 5.844 ppm (1H) (ABq, J$_{AB}$=10.2 Hz; the 5.744 peaks are further split into dd with J=2.8, 2.8 Hz).

$^{13}$C NMR (CDCl$_3$; 75.5 MHz) δ20.72, 20.93, 28.79, 63.35, 65.49, 66.72, 75.23, 89.02, 128.13, 129.67, 170.17, 170.57 ppm.

IR (KBr) 2976, 2935, 1746, 1392, 1370, 1235, 1183, 1100, 1044, 1025 cm$^{-1}$.

R=Ph (Reaction Time=8 hr. Yield=70%)

$^1$H NMR (CDCl$_3$; 300 MHz) δ1.976 (s,3H), 2.017 (s,3H), 4.10–4.30 (m,3H), 5.387 (d,J=11.4 Hz,1H), 5.698 (s,2H), 7.00–7.33 ppm (m,5H).

$^{13}$C NMR (CDCl$_3$; 75.5 MHz) δ20.54, 20.84, 62.66, 65.13, 67.85, 92.12, 117.10, 122.42, 127.14, 129.40, 130.06, 157.08, 170.06, 1740.46 ppm.

IR (KBr) 1744, 1598, 1589, 1491, 1371, 1222, 1187, 1096, 1076, 1047, 1029, 1005 cm$^{-1}$.

R=p-MeO—Ph (Reaction Time=12 hr. Yield=75%) mp (hexanes)=77°–77.5° C.

$^1$H NMR (CDCl$_3$; 300 MHz) δ2.023 (s,3H), 2.109 (s,3H), 3.774 (s,3H), 4.14–4.30 (m,3H), 5.376 (d,J=9.1 Hz,1H), 5.567 (s,1H), 6.007 (s,1H), 6.830 (2H) and 7.047 ppm (2H) (ABq,J$_{AB}$=9.0 Hz).

$^{13}$C NMR (CDCl$_3$; 75.5 MHz) δ20.61, 20.85, 55.77, 63.03, 65.60, 67.94, 94.23, 114.85, 115.11, 116.21, 118.90, 127.51, 130.08, 170.32, 170.75 ppm.

IR (KBr) 2958, 2934, 2922, 1741, 1507, 1380, 1270, 1255, 1243, 1227, 1184, 1053, 1037, 1010 cm$^{-1}$.

R=CH$_2$Ph (Reaction Time=80 min. Yield=95%)

$^1$H NMR (CDCl$_3$; 300 MHz) δ2.081 (s,3H), 2.102 (s,3H), 4.09–4.29 (m,3H), 4.601 (1H) and 4.809 (1H) (ABq,J$_{AB}$=11.7 Hz), 5.139 (s,1H), 5.334 (dd, J=9.4, 1.3 Hz,1H) 5.875 (ABq, 2H), 7.29–7.40 ppm (m,5H).

$^{13}$C NMR (CDCl$_3$; 75.5 MHz) δ20.63, 20.81, 63.19, 65.74, 67.50, 70.35, 93.83, 127.00, 128.56, 128.56, 129.46, 170.12, 170.59 ppm.

IR (KBr) 3032, 2953, 2937, 2904, 1743, 1454, 1436, 1405, 1370, 1227, 1186, 1151, 1137, 1101, 1038, 1026 cm$^{-1}$.

R=CH$_2$CH=CH$_2$ (Reaction Time=80 min. Yield=88%)

$^1$H NMR (CDCl$_3$; 300 MHz) δ2.086 (s,3H), 2.106 (s,3H), 4.05–4.30 (m,5H), 5.084 (s,1H), 5.212 (d,J=10.3 Hz, 1H), 5.28–5.35 (m,2H), 5.848 (1H) and 5.899 (1H) (ABq,J$_{AB}$= 10.3 Hz), 5.92–5.99 ppm (m,1H).

$^{13}$C NMR (CDCl$_3$; 75.5 MHz) δ20.73, 20.91, 63.00, 65.35, 67.05, 69.22, 93.65, 117.35, 127.86, 129.27, 134.27, 170.18, 170.62 ppm.

R=CH$_2$C(CH$_3$)$_3$ (Reaction Time=30 min. Yield=97%)

$^1$H NMR (CDCl$_3$; 300 MHz) δ0.931 (s,9H), 2.086 (s,3H), 3.133 and 3.481 (ABq,J$_{AB}$=8.8 Hz, 2H), 4.07–4.27 (m,3H), 4.985 (s,1H) 5.305 (d,J=9.5 Hz,1H), 5.850 and 5.859 (ABq, J$_{AB}$=10.5 Hz, 2H; the 5.850 ppm peaks are further split into dd with J=2.7 and 2.6 Hz).

$^{13}$C NMR (CDCl$_3$; 75.5 MHz) δ20.73, 20.91, 63.00, 65.35, 67.05, 69.22, 93.65, 117.35, 127.86, 129.27, 134.27, 170.18, 170.62 ppm.

R=OAc (Reaction time 24 h. Yield=81%) (20 mol % of acetic acid was used).

$^1$H NMR (CDCl$_3$; 300 MHz) δ2.082 (s,3H), 2.095 (s,3H), 2.098 (s,3H), 4.06–4.28 (m,3H), 5.368 (d,J=10.5 Hz, 1H), 5.850 and 6.011 (ABq, J$_{AB}$=10.6 Hz, 2H; the 5.850 ppm peaks are further split into dd with J=2.7 and 2.2 Hz), 6.294 ppm (s,1H).

SPECTROSCOPIC DATA FOR THIOL (RSH) ADDUCTS

R=Et (−78° to −55° C., Reaction Time=3.5 hr. Yield=35%)

$^1$H NMR (CDCl$_3$; 300 MHz) δ1.252 (t,J=7.1 Hz, 3H), 2.080 (s,3H), 2.099 (s,3H), 3.581 (1H) and 3.832 (1H) (ABqJ$_{AB}$=9.7 Hz; both sets of peaks are further split into dq with J=7.1, 7.1 Hz), 4.08–4.29 (m,3H), 5.043 (s,1H), 5.315 (dd, J=9.6, 1.3 Hz, 1H), 5.831 (1H) and 5.883 ppm (1H) (ABqJ$_{AB}$=10.3 Hz).

$^{13}$C NMR (CDCl$_3$; 75.5 MHz) δ15.31, 20.72, 20.92, 63.15, 64.30, 65.52, 67.02, 94.30, 128.09, 129.03, 170.20, 170.66 ppm.

IR (KBr) 2964, 2930, 1743, 1451, 1437, 1371, 1232, 1182, 1079, 1049 cm$^{-1}$.

R=i-Pr (−78° to 0° C. Reaction Time=6 hr. Yield=77%)

$^1$H NMR (CDCl$_3$; 300 MHz) δ1.337 (d,3H, J=6.8 Hz), 1.342 (d,3H,J=6.8 Hz), 2.085 (s,6H), 3.145 (dq,1H,J=6.8, 6.8 Hz), 4.15–4.38 (m,3H), 5.349 (d,1H, J=9.6 Hz), 5.638 (s,1H), 5.761 (1H) and 5.935 ppm (1H) (ABqJ$_{AB}$=10.1 Hz).

$^{13}$C NMR (CDCl$_3$; 75.5 MHz) δ20.66, 20.92, 23.88, 36.3, 63.14, 65.25, 66.93, 79.61, 126.74, 129.39, 170.21, 170.60 ppm.

IR (KBr) 2960, 2927, 2868, 1743, 1462, 1419, 1369, 1229, 1181, 1157, 1122, 1078, 1050 cm$^{-1}$.

R=t-Bu (−25° to 0° C., Reaction Time=2 hr. Yield=68%)

$^1$H NMR (CDCl$_3$; 300 MHz) δ1.404 (s,9H), 2.070 (s,3H), 2.080 (s,3H), 4.13–4.37 (m,3H), 5.325 (dd,1H,J=9.3, 1.8 Hz), 5.739 (d,1H, J=1.7 Hz), 5.753 (1H) and 5.902 ppm (1H) (ABqJ=10.9 Hz).

$^{13}$C NMR (CDCl$_3$; 75.5 MHz) δ20.70, 20.94, 31.51, 44.33, 63.22, 65.16, 66.84, 78.17, 126.61, 129.67, 170.30, 170.72 ppm.

IR (KBr) 2962, 1744, 1368, 1236, 1164, 1078, 1054 cm$^{-1}$.

By the same procedure, but using mevinolin (lovastatin) as a substrate rather than cholesterol, the resulting adduct in about 60% yield is Lovastatin 4,6-di-O-acetyl-2,3-dideoxy-α-D-erythro-hex-2-enopyranoside having the formula:

The reaction is carried out under mild conditions, e.g., preferably at room temperature, for one hour, using triacetyl D-glucal (1.0 equiv), iodine (20 mol %) in THF as the solvent.

R=Lovastatin (Reaction Time=1 h. Yield=55%)

$^1$H NMR (CDCl$_3$; 300 MHz) δ0.873 (t,J=7.5 Hz,3H), 0.892 (d,J=7.0 Hz, 3H), 1.074 (d,J=7.4 Hz, 3H), 1.105 (d,J=6.9 Hz, 3H), 2.091 (s,3H), 2.094 (s,3H), 3.99–4.05 (m,1H), 4.14–4.28 (m,3H), 4.29–4.34 (m,1H), 4.52–4.61 (m,1H), 5.134 (s,1H), 5.323 (dd,J=9.6, 1.3 Hz, 1H), 5.373 (d,J=2.7 Hz, 1H), 5.75–5.91 (m,2H), 5.909 (part of ABq, J$_{AB}$=11.1 Hz, 1H), 5.992 ppm (d,J=9.7 Hz, 1H).

$^{13}$C NMR (CDCl$_3$; 75.5 MHz) δ11.67, 13.92, 16.23, 20.70, 20.88, 22.85, 24.23, 26.79, 27.51, 30.77, 32.77, 33.22, 35.01, 35.73, 36.65, 37.46, 41.45, 62.98, 65.26, 67.38, 67.85, 68.65, 76.70, 93.12, 127.44, 128.44, 129.49, 129.72, 131.65, 132.94, 169.32, 170.07, 170.47, 176.39 ppm.

By the same procedure, but using either mephenesin or capsaicin as a substrate rather than mevinolin, the resulting adduct is mephenesin 4,6-di-O-acetyl-2,3-dideoxy-α-D-erythro-hex-2-enopyranoside and capsaicin 4,6di-O-acetyl-2,3-dideoxy-α-D-erythro-hex-2-enopyranoside, respectively.

R=Mephenesin (Reaction Time=1 h. Yield=85%)

$^1$H NMR (CDCl$_3$; 300 MHz) δ2.068 (s,3H), 2.071 (s,3H), 2.077 (s,3H), 2.080 (s,3H), 2.214 (brs,3H), 3.70–3.82 (m,3H), 3.99–4.40 (m,11H), 5.06–5.12 (m,1H), 5.28–5.39 (m,3H), 5.78–5.99 (m,4H), 6.81–6.91 (m,3H), 7.11–7.19 ppm (m,2H).

R=Capsaicin (Reaction Time=8 h. reflux in THF. Yield=60%)

$^1$H NMR (CDCl$_3$; 300 MHz) δ0.834 (d,J=6.6 Hz, 3H), 0.948 (d,J=6.7 Hz, 3H), 2.091 (s,3H), 2.093 (s,3H), 3.850 (s), 5.27–5.35 (m,2H), 5.45–5.90 (m,4H), 6.71–6.88 (m,3H).

Adducts with cholic acid or a cholic acid analog by this procedure are as follows:

Chenodeoxycholic Acid (chenodiol)

Conditions triacetyl D-glucal (2.0 equiv); iodine (20 mol %); THF, room temperature, 4 h Results diadduct (89%) chenodeoxycholic acid 3,7-di-(4,6-di-O-acetyl-2,3-deoxy-α-D-erythro-hex-2-enopyranoside).

Deoxycholic Acid

Conditions triacetyl D-glucal (2.0 equiv); iodine (20 mol %); THF, room temperature, 4 h Results diadduct (91%) chenodeoxycholic acid 3,12-di-(4,6-di-O-acetyl- 2,3-deoxy-α-D-erythro-hex-2-enopyranoside).

Cholic Acid

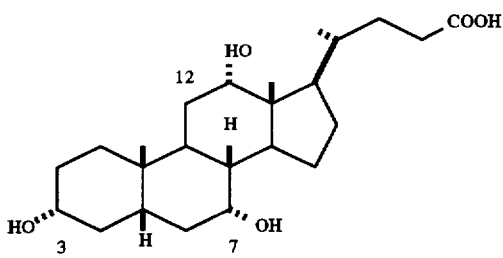

Conditions triacetyl D-glucal (3.0–5.0 equiv); iodine (20 mol %); THF, reflux, 8 h Results mixture of di- and triadducts (85%):
cholic acid 3,7-di-(DDH pyranoside);
cholic acid 3,12-di-(DDH pyranoside); and
cholic acid 3,7,12-tri-(DDH pyranoside).

An adduct with chloramphenicol by this procedure is as follows:

Chloramphicol

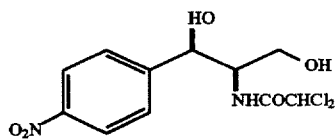

Conditions triacetyl D-glucal (2.0 equiv); iodine (20 mol %); THF, room temperature, 6 h Results diadduct (85%) chloramphenicol 1,3-di-(DDH pyranoside).

Having described the invention, the embodiments of the invention in which an exclusive property or privilege is claimed are defined as follows:

1. A composition comprising a 2,3-dideoxy-α-D-erythro-hex-2-enopyranoside derivative of acetaminophen and a pharmaceutically effective carrier.

2. The composition of claim 1 wherein said derivative is p-Acetoamidophenyl 6-O-acetyl-4-O-(2,3,4,6-tetra-O-acetyl-α-D-glucopyranosyl)-2,3-dideoxy-α-D-erythro-hex-2-enopyranoside.

3. The composition of claim 1, wherein said derivative is p-Acetoamidophenyl 4-O-(a-D-glucopyranosyl)-2,3-dideoxy-α-D-erythro-hex-2-enopyranoside.

4. The composition of claim 1, wherein said derivative is p-Acetoamidophenyl 6-O-acetyl-4-O-(2,3,4,6-tetra-O-acetyl-β-D-galactopyranosyl)-2,3-dideoxy-α-D-erythro-hex-2-enopyranoside.

5. The composition of claim 1, wherein said derivative is p-Acetoamidophenyl 4-O-(β-D-galactopyranosyl)-2,3-dideoxy-α-D-erythro-hex-2-enopyranoside.

6. A method of synthesizing a 2,3-dideoxy-α-D-erythro-hex-2-enopyranoside derivative of acetaminophen, comprising:

a) providing i) a reaction vessel, ii) 4-acetamidophenol, iii) a glycal selected from the group consisting of mono- and disaccharides having a 2,3-dideoxy-α-D-erythro-hex-2-enopyranoside moiety, and iv) a catalyst;

b) mixing said 4-acetamidophenol, said glycal, and said catalyst in said reaction vessel to create a mixture;

c) heating said mixture under conditions such that a 2,3-dideoxy-α-D-erythro-hex-2-enopyranoside derivative of acetaminophen is formed.

7. The method of claim 6, wherein said catalyst is a molecular diatomic halogen.

8. The method of claim 7, wherein said molecular diatomic halogen is molecular diatomic iodine.

* * * * *